United States Patent [19]

Kingston et al.

[11] Patent Number: 5,470,866
[45] Date of Patent: Nov. 28, 1995

[54] METHOD FOR THE CONVERSION OF CEPHALOMANNINE TO TAXOL AND FOR THE PREPARATION OF N-ACYL ANALOGS OF TAXOL

[75] Inventors: David G. I. Kingston, Blacksburg, Va.; Anthony A. Molinero, Ashland City, Tenn.; A. A. Leslie Gunatilaka, Blacksburg, Va.

[73] Assignee: Virginia Polytechnic Institute and State University, Blacksburg, Va.

[21] Appl. No.: 208,361

[22] Filed: Mar. 9, 1994

Related U.S. Application Data

[63] Continuation-in-part of Ser. No. 931,319, Aug. 18, 1992, Pat. No. 5,319,112.

[51] Int. Cl.[6] .................... C07D 305/14; A61K 31/335
[52] U.S. Cl. .................... 514/376; 514/449; 548/226; 549/510; 549/511
[58] Field of Search .................... 549/510, 511; 514/449, 376; 548/226

[56] References Cited

U.S. PATENT DOCUMENTS

| | | | |
|---|---|---|---|
| 4,206,221 | 6/1980 | Miller et al. | 424/278 |
| 4,814,470 | 3/1989 | Colin et al. | 549/510 |
| 4,857,653 | 8/1989 | Colin et al. | 549/511 |
| 4,924,012 | 5/1990 | Colin et al. | 549/510 |
| 5,015,744 | 5/1991 | Holton | 549/510 |
| 5,059,699 | 10/1991 | Kingston et al. | 549/511 |

FOREIGN PATENT DOCUMENTS 0400971  12/1990  European Pat. Off. .

OTHER PUBLICATIONS

Kingston et al., "Modified Taxols, 7[1]. A Method for the Separation of Taxol and Cephalomannine", J. Nat. Prod., 55, 259–261 (1992).

Georg et al., "Schotten–Baumann Acylation of N–Debenzoyltaxol; An Efficient Route to N-Acyl Taxol Analogues and Their Biological Evaluation", Bioorg. Med. Chem. Lett., 4, 335–338 (1994).

Georg et al., "Novel Biologically Active Taxol Analogues: Baccatin III 13-(N-(p-Chlorobenzoyl)-(2'R, 3'S)-3'phenylisoserinate) and Baccatin III 13-(N-Benzoyl-(2'R,3'S)-3'(p-chlorophenyl)isoserinate)", Bioorg. Med. Chem. Lett., 2, 295–298 (1992).

Kingston, et al., "The Chemistry of Taxol, A Clinically Useful Anti–Cancer Agent", J. Nat. Prod., 53, 1–12 (1990).

Deutsch et al., "Synthesis of Congeners and Prodrugs 3. Water–Soluble Prodrugs of Taxol With Potent Antitumor Activity", J. Med. Chem., 32, 788–792 (1989).

Mangatal et al., "Application of the Vicinal Oxyamination Reaction with Asymmetric Induction to the Hemisynthesis of Taxol and Analogues", Tetrahedron, 45, 4177–4190 (1989).

Denis et al., "A Highly Efficient, Practical Approach to Natural Taxol", J. Am. Chem. Soc., 110, 5917–5919 (1988).

Magri et al., J. Org. Chem., 51, 30–39, (1986).

(List continued on next page.)

*Primary Examiner*—C. Warren Ivy
*Assistant Examiner*—Ba K. Trinh
*Attorney, Agent, or Firm*—Popham, Haik, Schnobrich & Kaufman, Ltd.

[57] ABSTRACT

The natural product cephalomannine can be converted to the important anticancer natural product taxol by a simple process involving the steps of dihydroxylation to give cephalomannine-diols, diol cleavage, benzoylation at the 2'-position and reaction with a 1,2-diamine. The same process when applied to mixtures of taxol and cephalomannine makes it possible to separate taxol from cephalomannine-diols by simple flash-chromatography after the dihydroxylation step. If the benzoylation step is avoided in the above sequence of conversions, the process leads to the free amine (N-debenzoyltaxol). In addition, the selection of an acylating reagent other than that with the benzoyl group for acylation of the free amine (N-debenzoyltaxol), allows the preparation of taxol analogs with other N-acyl substituents.

22 Claims, 7 Drawing Sheets

OTHER PUBLICATIONS

Mathew et al., "Synthesis and Evaluation of Some Water-Soluble Prodrugs and Derivatives of Taxol with Antitumor Activity", J. Med. Chem., 35, 145–151 (1992).

Swindell et al., "Biologically Active Taxol Analogs With Deleted A-Ring Side-Chain Substituents and Variable C-2' Configurations", J. Med. Chem., 34, 1176–1184 (1991).

Powell et al., "Cephalomannine; A New Antitumor Alkaloid for Cephalotaxus mannii", Chem. Comm., 102–104 (1979).

McGuire et al., "Taxol: A Unique Antineoplastic Agent with Significant Activity in Advanced Ovarian Epithelial Neoplasms", Ann. Int. Med., 111, 273–279 (1989).

Holmes et al., "Phase II Trial of Taxol, an Active Drug in the Treatment of Metastatic Breast Cancer", J. Nat. Can. Inst., 24, 1791–1805 (1991).

Rowinsky et al., "Taxol: Twenty Years Later, the Story Unfolds", J. Nat. Can. Inst., 24, 1778–1781 (1991).

Guerritte-Voegelein et al., "Chemical Studies of 10-Deacetyl Baccatin III. Hemisynthesis of Taxol Derivatives", Tetrahedron, 42, 4451–4460 (1986).

Kingston, "The Chemistry of Taxol", Pharmac. Ther., 52, 1–34 (1991).

Ringel et al., "Studies with RP 56976 (Taxotere): A Semisynthetic Analogue of Taxol", J. Nat. Can., Inst., 4, 288–291 (1991).

Gueritte-Voegelein et al., "Relationships Between the Structure of Taxol Analogues and Their Antimitotic Activity", J. Med. Chem., 34, 992–998 (1991).

Miller et al., "Antileukemic Alkaloids from Taxus Wallichiana Zucc.", J. Org. Chem., 46, 1469–1474 (1981).

Shiozaki et al., "Cleavage and Some Modifications of the 7-Amide Group of the Cephamycins", Tetrahedron, 36, 2735–2740 (1980).

Shiozaki et al., "A New Method for Cleavage 7-Amide Group of Cephalosporins", Tetrahedron Left., 46, 4059–4062 (1977).

Kingston, et al., "The Taxane Diterpeniods," in Progress in the Chemistry of Organic Natural Products, 61, 1–206, Springer-Verlag (1993).

Georg, et al., "Synthesis of Biologically Active Taxol Analogues with Modified Phenylisoserine Side Chains," J. Nat. Prod., 35, 4230–4237 (1993).

Commercon, et al., "Improved Protection and Esterification of a Precursor of the Taxotere® and Taxol Side Chains," Tetrahedron Lett. 5185–5188 (1992).

Jitrangsri, Chote, "Approaches to the Synthesis of Modified Taxols", Ph. D. dissertatim VPI & SU, Aug. 1986 pp. 145–146.

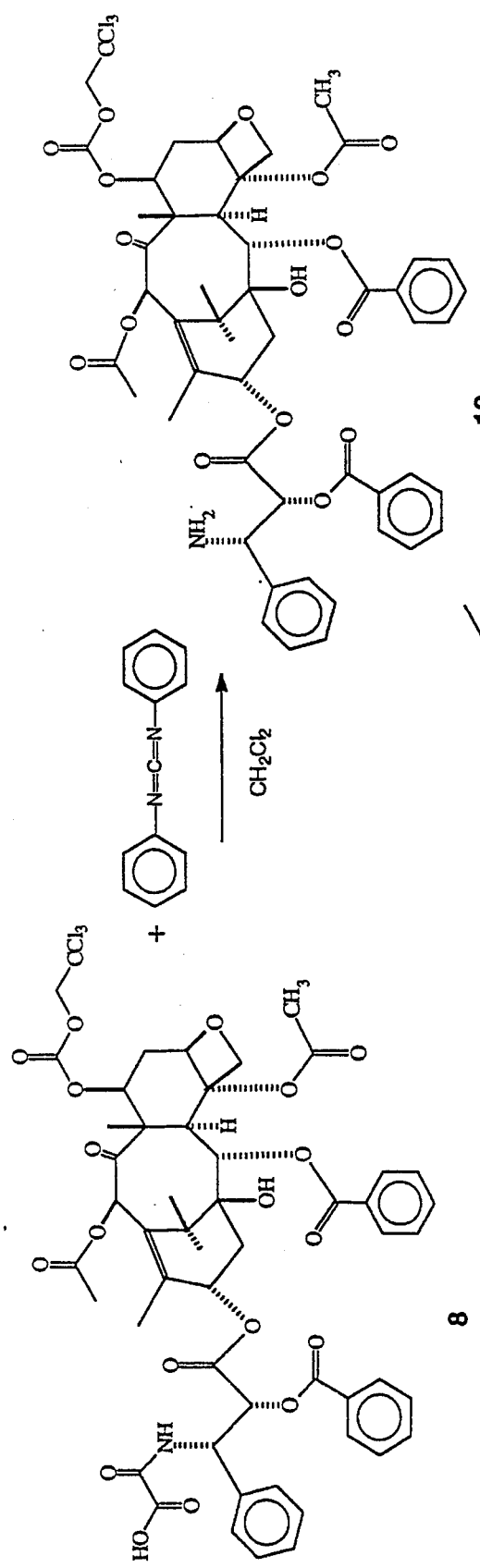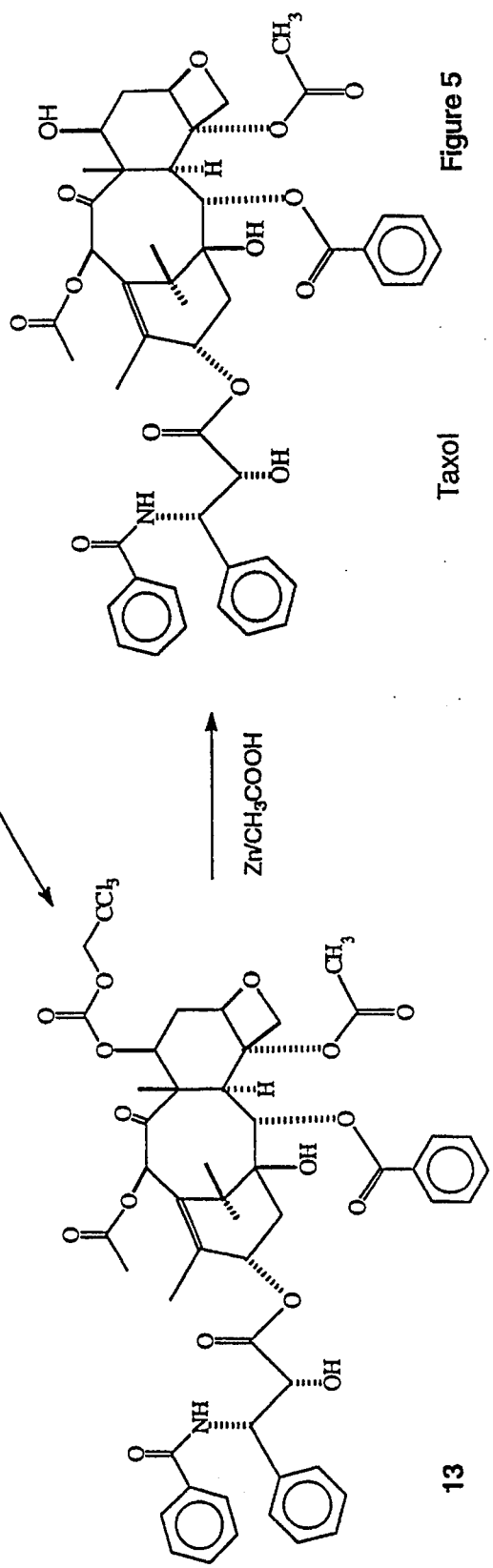
Figure 5

METHOD FOR THE CONVERSION OF CEPHALOMANNINE TO TAXOL AND FOR THE PREPARATION OF N-ACYL ANALOGS OF TAXOL

This application is a Continuation-In-Part of U.S. patent application Ser. No. 07/931,319, filed Aug. 18, 1992, now U.S. Pat. No. 5,319,112.

FIELD OF THE INVENTION

The present invention relates to taxol, taxol congeners, taxol analogues, and methods for making same. The invention relates more particularly to the synthesis of taxol or taxol congeners from natural products having portions of the taxol structure.

BACKGROUND OF THE INVENTION

Taxol is a naturally occurring diterpenoid which has demonstrated great potential as an anti-cancer drug. Taxol, shown below as compound 1, can be isolated from the bark of the western yew, *Taxus brevifolia*, and is also found in several other yew species such as *T. baccata* and *T. cuspidata*. For further information regarding taxol, see Kingston et al., U.S. Pat. No. 5,059,699. All patents, articles, and other documents cited herein are incorporated by reference as if reproduced in full below.

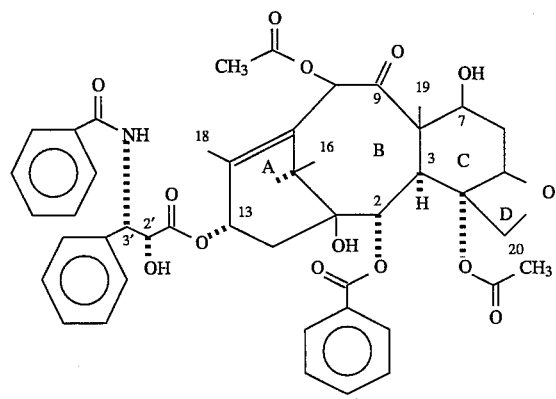

Taxol almost always co-occurs with the closely related compound cephalomannine, shown below as compound 2. Due to their close structural similarity, the separation of taxol from cephalomannine is a very difficult one. See Wani et al., "Plant Antitumor Agents. VI. The Isolation and Structure of Taxol, A Novel Antileukemic and Antitumor Agent from *Taxus brevifolia*," *J. Am Chem. Soc.* 93, 2325(1971); Powell et al., "Cephalomannine; A New Antitumor Alkaloid from *Cephalotaxus mannii*," *J. Chem. Soc. Chem. Commun.* 102 (1979); Miller et al., "Antileukemic Alkaloids from *Taxus wallichiana Zucc*," *J. Org. Chem.* 46, 1469 (1981). The only practical methods developed thus far for the separation involve careful and demanding chromatography or dihydroxylation of the taxolcephalomannine mixture followed by flash chromatography affording pure taxol, and cephalomannine-diols (a mixture of diastereomers, shown below as compound 29). See Kingston et al., "Modified Taxols, 7. A Method for the Separation of Taxol and Cephalomannine.") *Nat. prod.* 55, 259 (1992).

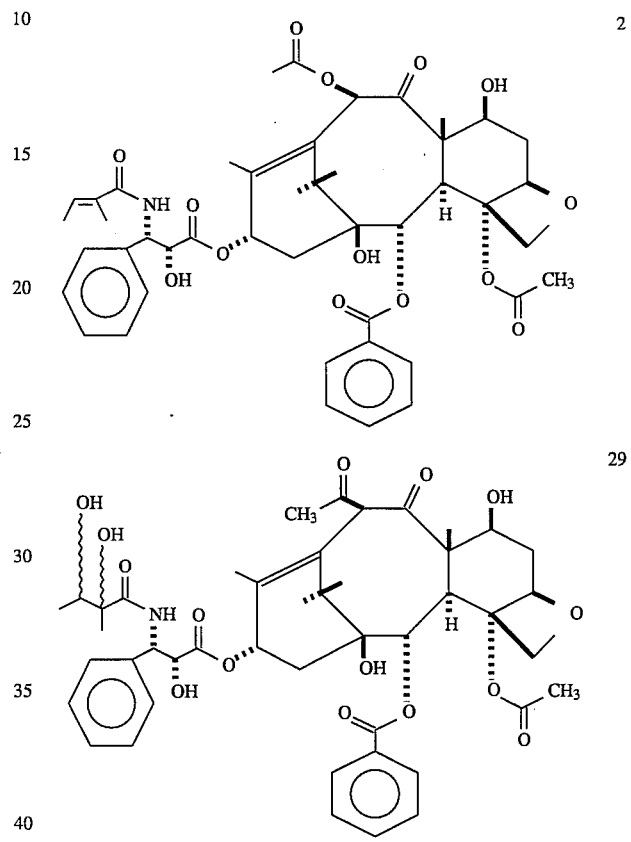

Since taxol is very scarce, a procedure to convert the resulting cephalomannine-diols to taxol would prove valuable because it would increase the supply of taxol. A method to make taxol from cephalomannine while avoiding the need to separate cephalomannine from taxol, would also be desirable.

No previous work on a direct conversion of cephalomannine to taxol has been reported. An indirect route is available through the work of Magri et al., in *Journal of Organic Chemistry*, Vol. 51, p. 3239, 1986, who reported that taxol can be converted to baccatin III, shown below as compound 3, by treatment with tetrabutylammonium borohydride in dichloromethane. It has been discovered that this process works equally well with cephalomannine, so a pathway exists to prepare baccatin III 3 from cephalomannine.

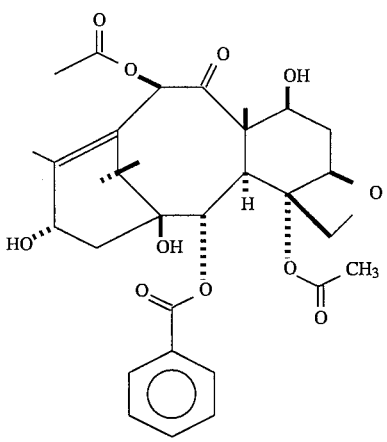

3

Baccatin III 3 can be converted to taxol by one of several published pathways. See, for example, Holton, R., "Method for Preparation of Taxol Using an Oxazinone," U.S. Pat. No. 5,015,744; Denis et al., "Highly Efficient Practical Approach to Natural Taxol," *J. Am. Chem. Soc.* 110, 5917(1988); Mangatal et al., "Application of the Vicinal Oxyamination Reaction with Asymmetric Induction to the Hemisynthesis of Taxol and Analogues," *Tetrahedron* 45, 4177(1989); Denis et al., "Process for Preparing Taxol," U.S Pat. No. 4,924,011 (1990); Colin et al., "Process for the Preparation of Taxol and 10-deacetyltaxol," U.S. Pat. No. 4,857,653 (1989); Ojima et al., "New and Efficient Approaches to the Semisynthesis of Taxol and its C-13 Side Chain Analogs by Means of b-lactam Synthon Method," *Tetrahedron*, 48, 6985–7012 (1992); Georg et al., "An Efficient Semisynthesis of Taxol from (3R,4S)-N-Benzoyl-3-[(t-butyldimethylsilyl)oxy]-4-phenyl-2-azetidinone and 7-(Triethylsilyl)baccatin III," *Bioorg. Med. Chem. Lett.*, 3, 2467–2470 (1993); Denis et al, "Taxotere by Esterification with Stereochemically "Wrong" (2S,3S)-Phenylisoserine Derivatives," *Tetrahedron Lett.*, 35, 105–108 (1994); Commercon et al., "Improved Protection and Esterification of a Precursor of the Taxotere and Taxol Side Chains," *Tetrahedron Lett.*, 33, 5185–5188 (1992).

Hence, cephalomannine can be converted to taxol through baccatin III 3, by treatment of cephalomannine with, by way of non-limiting example, tetrabutylammonium borohydride in the presence of dichloromethane. However, this process requires the synthesis of the β-phenylisoserine side-chain of taxol in enantiomerically pure form, and the coupling of the side-chain to baccatin III 3 does not proceed quantitatively.

Because of the promising clinical activity of taxol against various types of cancer, the preparation of analogues of taxol is an important endeavor, especially in view of the previously mentioned limited supply of taxol. See McGuire et al., "Taxol: A Unique Antineoplastic Agent with Significant Activity in Advanced Ovarian Epithelial Neoplasms," *Ann, Intern. Med.* 111: 273–279 (1989); Holmes et al., "Phase II Trials of Taxol, an Active Drug in the Treatment of Metastatic Breast Cancer," *J. Natl. cancer Inst*, 83: 1797–1805 (1991).

It is believed that the preparation of taxol analogues will result in the synthesis of compounds with comparable or greater potency than taxol (thus reducing the need for the drug), superior bioavailability, or having less undesirable side effects. Indeed, the synthesis of the taxol analogue taxotere, which differs from taxol only in the nature of the N-acyl substituent and the absence of the 10-acetyl group, indicates the usefulness of this approach, since taxotere is reported to be approximately twice as active as taxol in some assays (although taxol is believed to be more effective in other systems than taxotere). See Guéritte-Voegelein et al., "Chemical Studies of 10-Deacetylbaccatin III. Hemisynthesis of Taxol Derivatives," *Tetrahedron* 42: 4451–4460 (1986); Ringel et al., "Studies with RP56976 (Taxotere) A Semisynthetic Analogue of Taxol," *J. Natl Cancer Inst.* 83: 288–291 (1991).

A large number of taxol analogs have antitumor properties as shown by their ability to inhibit the disassembly of microtubules. See "Relationships between the Structure of Taxol Analogues and Their Antimitotic Activity," *Journal of Medicinal Chemistry*, Vol. 34, pp. 992–998 (1991); "Biologically Active Taxol Analogues with Deleted A-Ring Side Chain Substituents and Variable C-2' Configurations," *Journal of Medicinal Chemistry*, Vol. 34, pp. 1176–1184, (1991); "Synthesis and Evaluation of Some Water-Soluble Prodrugs and Derivatives of Taxol with Antitumor Activity," *Journal of Medicinal Chemistry*, Vol. 35, pp. 145–151, (1992). The foregoing articles demonstrate the effectiveness of taxol analogs as antitumor agents.

Nonetheless, many taxol analogs have shown reduced biological activity when compared to taxol. Thus, there remains a need for taxol derivatives or compounds having similar biological activities to taxol. There is a corresponding need for methods to prepare taxol derivatives and taxol congeners.

There is also a need to prepare taxol from naturally occurring mixtures, and more particularly, there is a need to convert cephalomannine, or mixtures comprising cephalomannine, to taxol.

There is also a need for better methods of treating cancer, and more particularly of treating cancer with taxol analogs.

OBJECTS OF THE INVENTION

Therefore, it is a primary object of the present invention to convert-cephalomannine, or a mixture comprising cephalomannine, to taxol.

It is another object of the present invention to prepare analogs of taxol.

It is a further object of this invention to develop a new method for preparing taxol and taxol congeners.

It is yet another object of the present invention to prepare intermediates that can be directly converted to taxol or taxol congeners.

It is a further object of the present invention to use taxol analogs to treat cancer.

It is a still further object of this invention to produce taxol from a naturally occurring mixture.

It is yet another object of the present invention to develop taxol analogs that have antineoplastic activities that are similar to or better than taxol.

SUMMARY OF THE INVENTION

These and other objects are achieved by the present invention as more fully described herein by reference to preferred non-limiting embodiments. In a first embodiment, a mixture of cephalomannine 2 and taxol 1 is converted to taxol 1 by substituting the 2-methyl-2-butenoyl moiety on the C-13 side chain of cephalomannine with a benzoyl group; more specifically, a preferred process comprises the steps of (1) hydrogenation, (2) benzoylation, (3) protection of the C-7 hydroxyl group as its trichloroethyloxycarbonyl ("troc") or other protecting group (4) reaction with oxalyl chloride followed by addition of water, (5) reaction with diphenylcarbodiimide, and (6) removal of the protective group by reduction with zinc and acetic acid (troc) or hydrolysis (TES). In a second embodiment, pure cephalomannine is converted to pure taxol by the same reaction sequence.

In a third embodiment, either taxol, taxol congeners, or cephalomannine can be converted to an N-debenzoyl-N-(alkyloxalate) analog or an N-debenzoyl-N-(N'-alkyloxamido) analog or the corresponding aryl analogs by the sequence of (1) hydrogenation (if necessary), (2) protection of the C-2' and C-7 hydroxyl groups as their 2,2,2-trichloroethyloxycarbonyl ("troc") or other protecting group derivative, and (3) reaction with oxalyl chloride followed by the addition of an appropriate alcohol or amine. The protective groups can be subsequently removed.

In a fourth embodiment, either taxol, taxol congeners or hydrogenated cephalomannine can be converted to any desired N-acyl analog by the sequence of (1) acylation with a desired acylation reagent, (2) protection of the C-7 hydroxyl group as its 2,2,2-trichloroethyloxycarbonyl ("troc") or other protecting group derivative (3) reaction with oxalyl chloride followed by addition of water, (4) reaction with diphenylcarbodiimide, during which the acyl at C-2' migrates to the amino group at the 3' position, and (5) removal of the protecting group at C-7.

In a fifth embodiment an intermediate, useful for its ability to be directly converted to taxol or taxol congeners, can be prepared from taxol, taxol congeners or hydrogenated cephalomannine by the sequence of (1) acylation, (2) protection of the C-7 hydroxyl group as its troc or other protecting group derivative, and (3) reaction with oxalyl chloride.

In a sixth embodiment, antineoplastic, N-oxalyl-containing taxol derivatives are prepared.

In a seventh embodiment, cephalomannine is converted to taxol by a process comprising: the oxidation of the tigloyl group (2-methyl-2-butenoyl) at the C-3' nitrogen of cephalomannine to a pyruvyl group (2-oxopropanoyl), benzoylation of the C-2' hydroxyl and removal of the pyruvyl group by reaction with a compound having adjacent amine groups.

In an eighth embodiment, cephalomannine is converted to N-debenzoyltaxol 30 by excluding the benzoylation step in the above-described seventh embodiment.

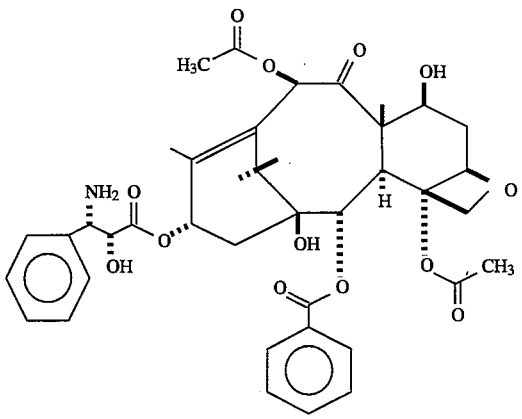

In a ninth embodiment, cephalomannine is converted to any desired N-acyl analog by substituting the desired acyl group for the benzoyl group in the above-described eighth embodiment or by simple acylation of N-debenzoyltaxol with a desired acylating agent.

In an tenth embodiment, taxol analogs are prepared wherein a substituent at the C-3' position has the formula:

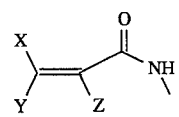

wherein Z is hydrogen or halogen, X is hydrogen, halogen or a lower alkyl, and Y is hydrogen or a lower alkyl.

DEFINITIONS

The terms used herein have the meanings as conventionally used in the chemical arts, unless the meaning is clearly indicated to be otherwise either by context or by specific language of the present disclosure. Definitions incorporate those used in standard texts, such as but not limited to Grant & Hackh's *Chemical Dictionary*, 5th edition, McGraw-Hill, 1987.

Taxol analogs are broadly defined herein as those analogs having the taxane tetracyclic nucleus with an ester substituent at the C-13 position. These analogs may include substitution at the C-2, C-4, C-7, C-10, C-2' and C-3' positions by substituents which may include, but are not limited to H, hydroxy, alkoxy, amido, and ester ($RCO_2$) wherein R is hydrogen, an alkali metal, an alkyl, an alkenyl, an alkynyl, an amino, or an aryl.

In the present invention the term iminio ion refers to the moiety:

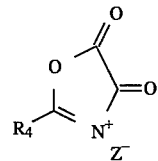

wherein $Z^-$ is a counterion, preferably but not limited to $Cl^-$.

The term alkyl refers to straight-chain or branched hydrocarbons which when incorporated into taxol compounds do not substantially destroy the properties of chemical stability, water solubility and biological activity; and in some preferable embodiments alkyl refers to the lower alkyls containing from one to six carbon atoms in the principal chain and up to 10 carbon atoms; the lower alkyls may be straight or branched chain and include methyl, ethyl, propyl, isopropyl, butyl, isobutyl, tert-butyl, and the like.

The term substituted alkyl refers to groups which do not substantially destroy the properties of water solubility, chemical stability and biological activity including, but not limited to, the alkyl groups discussed above which have substituents such as halo, e.g., chloro, bromo; nitro; sulfate; sulfonyloxy; carboxy; carboxylate, e.g., $—COO^{31}$; phosphate, e.g., $—OP(O)(OH)_2$, $—OP(O)(OR)(OH)$, $—OP(O)_2(OH)^-$, and the like; carbo-lower-alkoxy, e.g., carbomethoxy, carbethoxy; amino; mono- and di-lower-alkylamino, e.g., methylamino, dimethylamino, carboxamide; sulfonamide; diethylamino, methylethylamino; amide; alkylsilyl, siloxy, lower-alkoxy, e.g., methoxy, ethoxy; lower-alkanoyloxy, e.g., acetoxy; alkenyl, alkynyl; aryl; aryloxy; and combinations of these, e.g., alkylbenzenesulfonates.

The term substituted aryl refers to aryls with the same substituents discussed above for the substituted alkyls and also includes, but is not limited to, lower alkyl, e.g. methyl, ethyl, butyl, etc., provided the substituents do not substantially destroy the properties of chemical stability, water solubility, and biological activity.

In preferred embodiments, the terms alkyl, substituted alkyl, alkenyl (including substituted alkenyls), alkynyl (including substituted alkynyls), aryl, substituted aryl, etc. refer to groups composed of less than 20 carbon atoms and less than 25 total atoms other than hydrogen.

DESCRIPTION OF THE DRAWINGS

FIG. 5 illustrates a further step in the conversion of cephalomannine to taxol wherein reaction of the oxamic acid derivative with diphenylcarbodiimide, followed by removal of the protecting group by treatment with zinc and acetic acid produces taxol.

Figure 1:
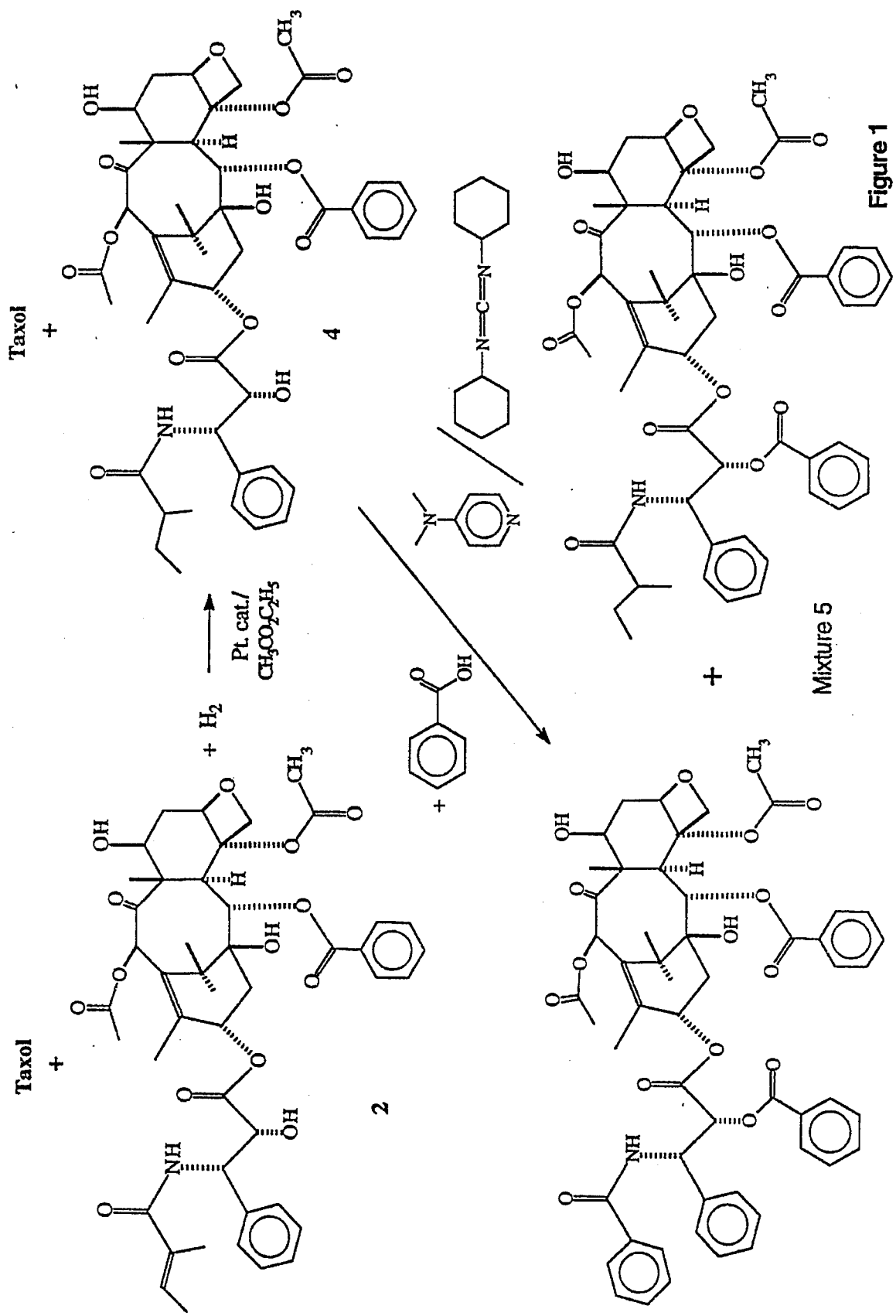
FIG. 1 illustrates steps in a preferred embodiment of the present invention involving the conversion of cephalomannine to taxol wherein a mixture of cephalomannine and taxol is hydrogenated and the hydroxyl group at the C-2' position is benzoylated.
Figure 2:
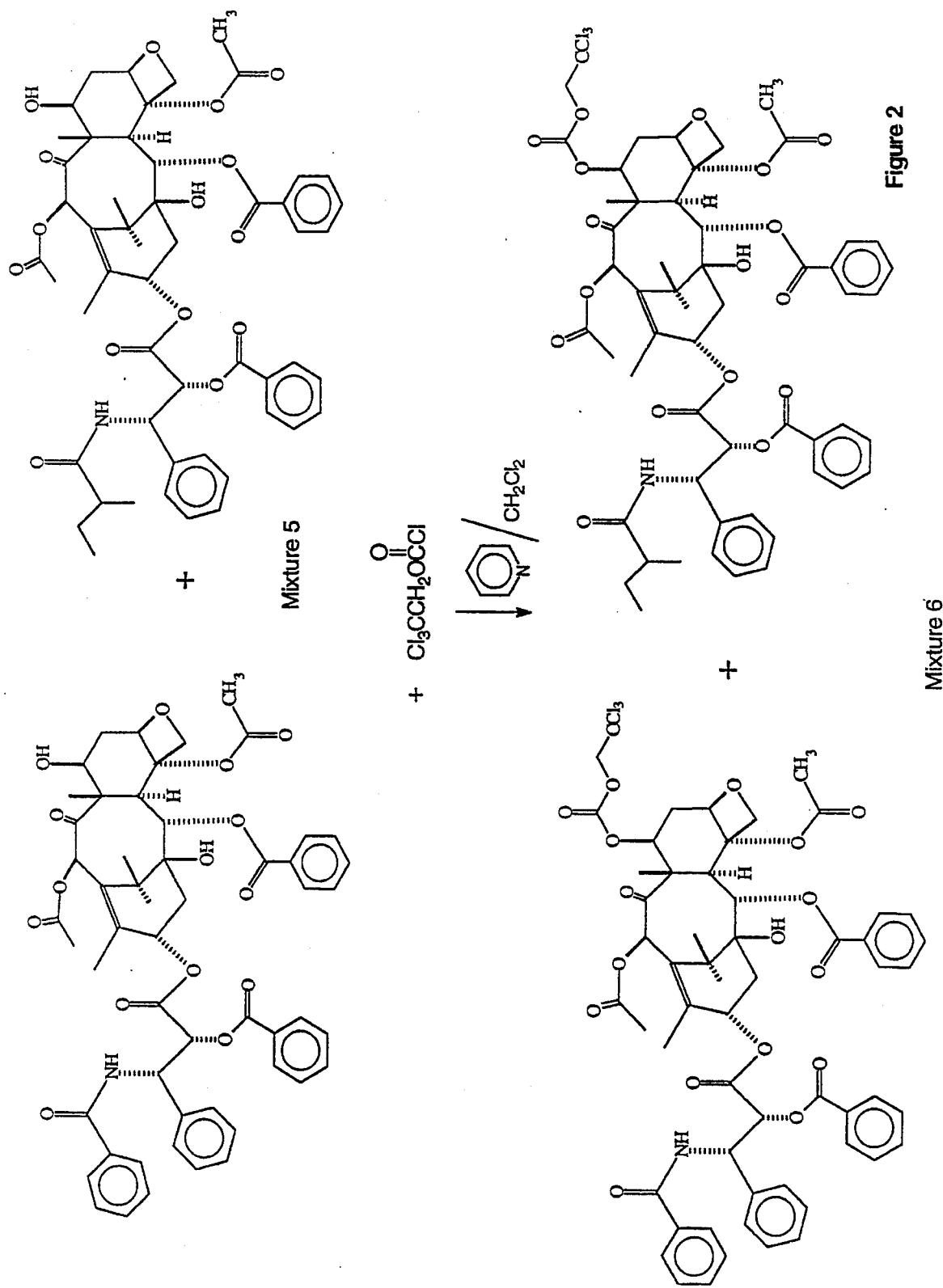
FIG. 2 illustrates a further step in the conversion of cephalomannine to taxol wherein the hydroxyl group at the C-7 position is protected by the reaction with 2,2,2-trichloroethyloxycarbonyl chloride.
Figure 3:
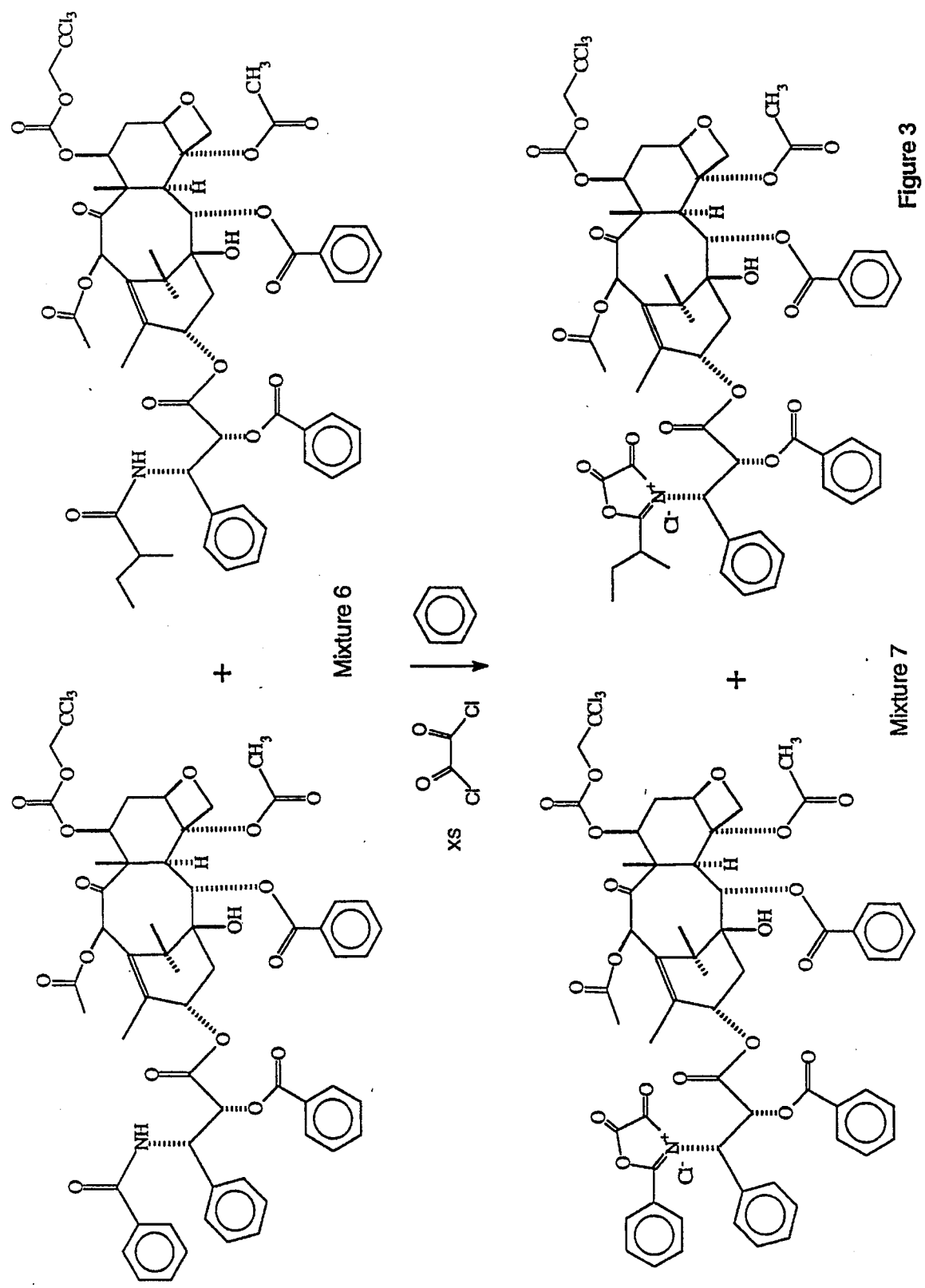
FIG. 3 illustrates a further step in the conversion of cephalomannine to taxol wherein an iminio salt is formed by the addition of oxalyl chloride.
Figure 4:
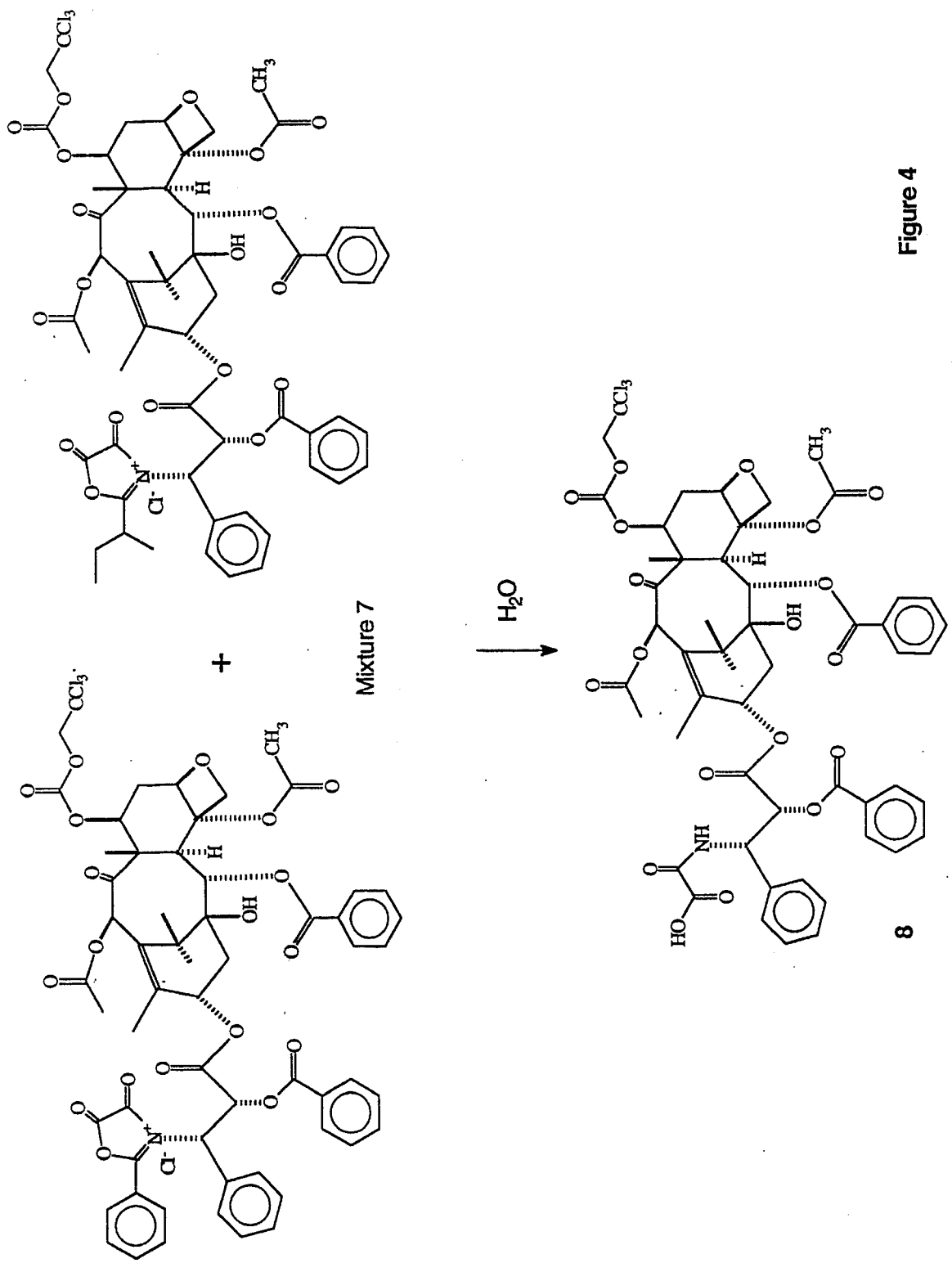
FIG. 4 illustrates a further step in the conversion of cephalomannine to taxol wherein an oxamic acid derivative is formed by the addition of water.
Figure 6:
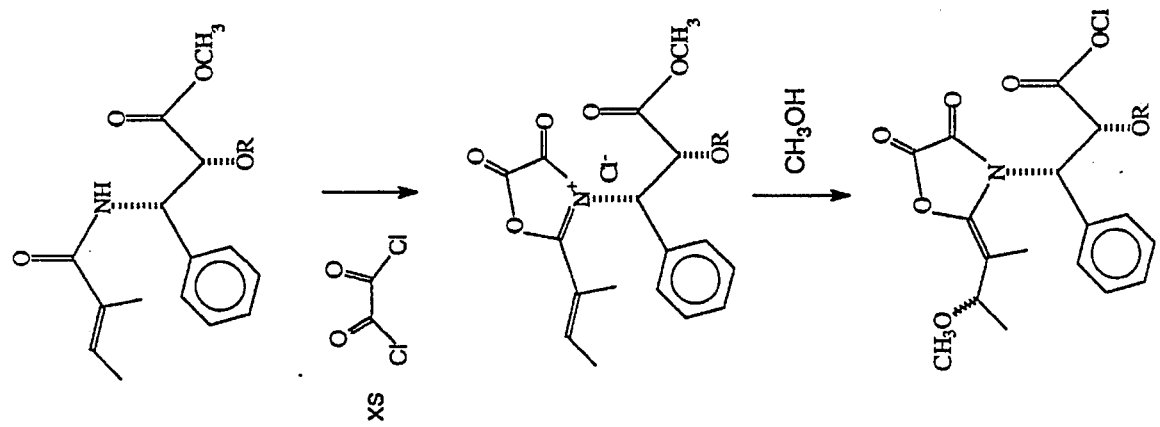
FIG. 6 illustrates a reaction using a model compound, which demonstrates the formation of a stable oxalyl heterocyclic derivative of taxol.

DETAILED DESCRIPTION OF THE INVENTION CONVERSION OF A MIXTURE OF CEPHALOMANNINE AND TAXOL TO TAXOL

With reference to FIGS. 1–5, a mixture of cephalomannine 2 and taxol 1 (about 1:1) is hydrogenated at room temperature over a platinum catalyst in ethyl acetate solution to give a mixture of taxol and dihydrocephalomannine 4 in quantitative yield. Compound 4 below

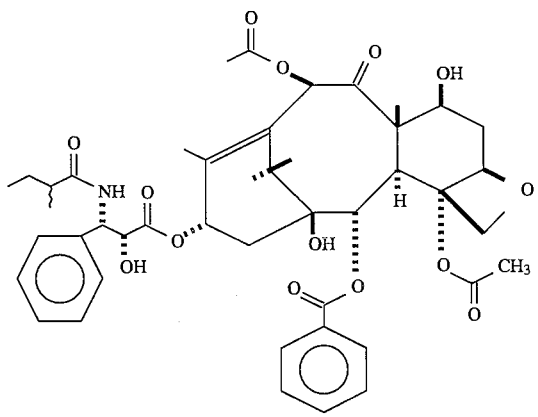

is a mixture of diastereomers at the 2"-position. The mixture was then benzoylated at the 2'-position by treatment with one equivalent of benzoic acid in the presence of an activating agent, which in a preferred embodiment comprises dicyclohexylcarbodiimide and 4-dimethylaminopyridine to yield a mixture of 2'-benzoates 5. Mixture 5, comprising the compounds 5 and 5', was then

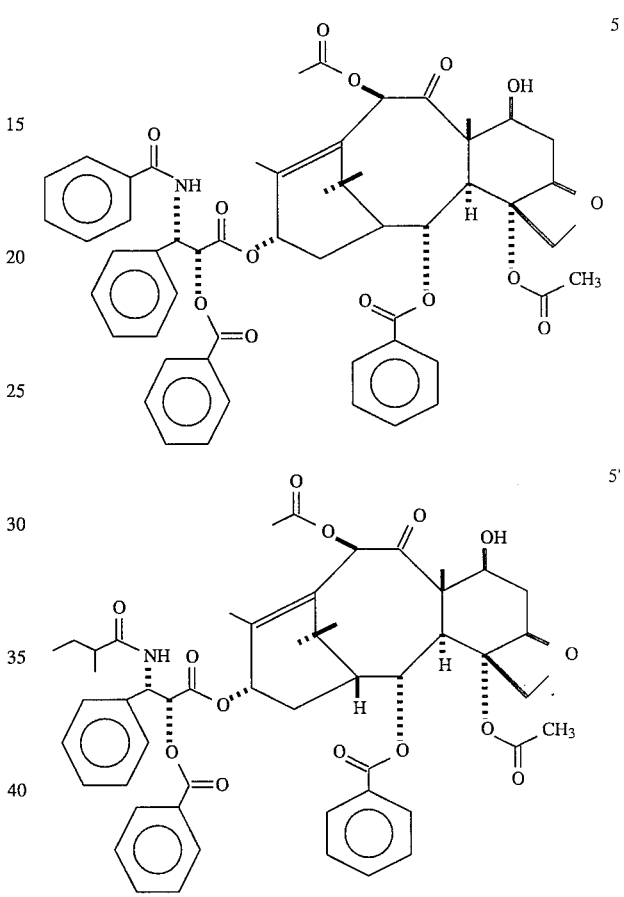

converted to its 7-trichloroethyl oxycarbonyl derivative 6, shown below by reaction with 2,2,2-trichloroethyloxycarbonyl chloride and pyridine in methylene chloride. Purification of mixture 6 by flash chromatography gave a purified mixture in 85% yield based on the original mixture.

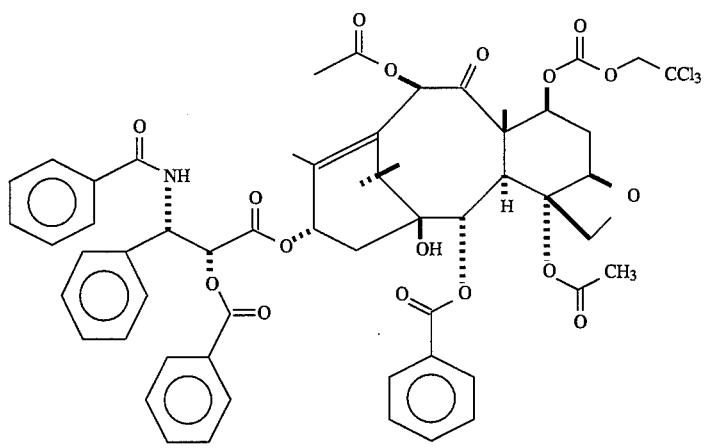
6
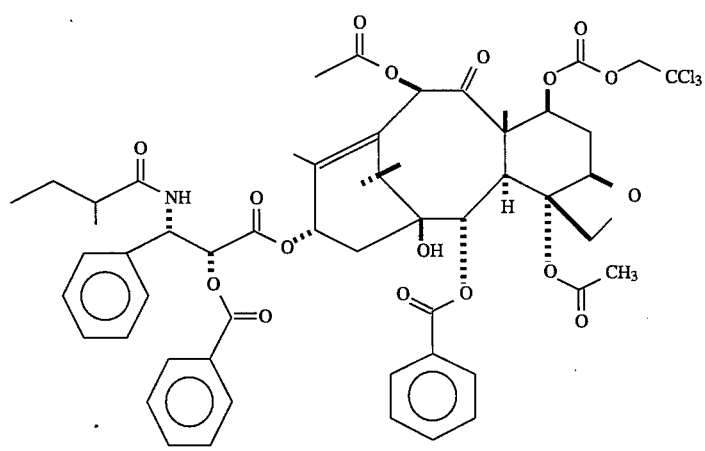
6'
Reaction of mixture 6 with excess oxalyl chloride at room temperature in benzene gave the mixture of iminio compounds 7 and 7' below.
7

-continued

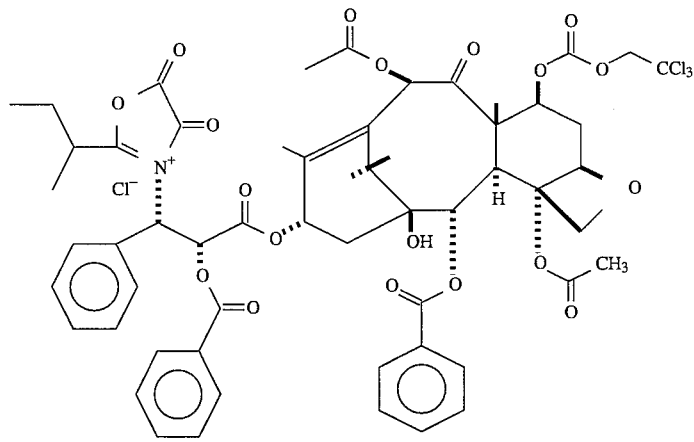

Compounds 7 and 7' appeared as a white crystalline precipitate over a period of 18 hours if the reaction was cooled, but were also formed in solution over 5 hours at room temperature. More information on the reaction of amides with oxalyl chloride can be found in Chiozaki et al. "A New Method for the Cleavage of 7-Amide Group of Cephalosporins," *Tetrahedron Letters* 46, 4059 (1977). Reaction of mixture 7 with water yielded the oxamic acid derivative 8 as a single pure substance in 65% yield from mixture 6.

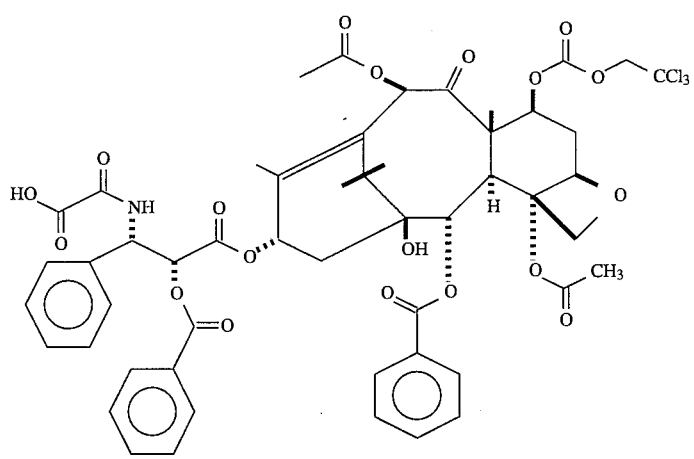

If the cephalomannine portion of the mixture is not hydrogenated first, reaction takes a different course. This can be illustrated by a model compound. Thus, treatment of the methyl ester 9 (R=PhCO) with oxalyl chloride yielded the iminium salt 10. Reaction of 10 with methanol, however, yielded in part the ether 11, formed by Michael addition of methanol to the αβ-unsaturated iminium salt. Similarly reaction of the nonhydrogenated cephalomannine-iminio ion with water would not form the oxamic acid derivative in good yield.

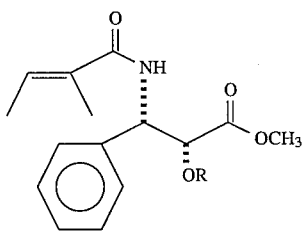

-continued

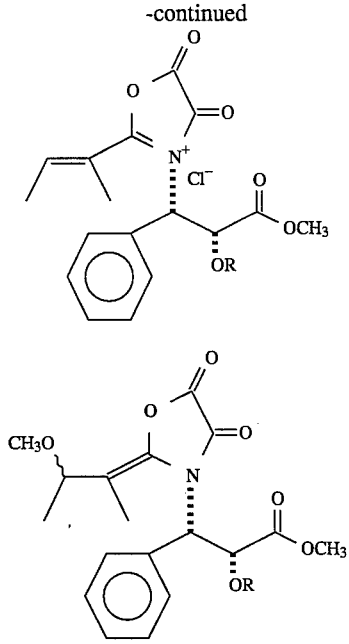

Conversion of oxamic acid 8 to taxol is accomplished by treatment with diphenylcarbodiimide. For more information on this type of reaction, see Shiozaki et al. in "Cleavage and Some Modifications of the 7-Amide Group of the Cephamycins," *Tetrahedron* 36, 2735 (1980), which discusses reaction of compounds with an oxamic acid moiety with diphenylcarbodiimide. Thus reaction of 8 with diphenylcarbodiimide in methylene chloride for 96 hours at room temperature yielded the protected taxol derivative shown below as 13. It is believed that the reaction proceeds initially to produce the amino taxol derivative shown as 12 in FIG. 5, and that O-acyl→N-acyl transfer occurs spontaneously to produce 13. Conversion of 13 to taxol 1 was achieved by treatment with zinc and acetic acid, as previously described for similar compounds.

ozonolysis of cephalomannine (see Powell et al., "Cephalomannine; A New Antitumor Alkaloid from *Cephalotaxus mannii*," *J. Chem. Soc. Chem. Commun.* 102 (1979), or, more preferably, in a higher yield two step process, by conversion of cephalomannine to cephalomannine diols by a literature method (see Kingston et al., "Modified Taxols, 7. A Method for the Separation of Taxol and Cephalomannine," *J. Nat. Prod.*, 55, 259 (1992)), followed by oxidation with sodium periodate. Although benzoylation may be conducted at any stage, in the embodiment illustrated in FIG. 7, benzoylation of the C-2' hydroxyl by reaction with benzoic acid in the presence of dicyclohexylcarbodiimide and 4-dimethylaminopyridine follows the oxidation step to yield 2-benzoyl-3-N-debenzoyl-3-N-pyruvyl-taxol, 32. Compound 32 is then reacted with 1,2-phenylenediamine in the presence of molecular sieves (3 Å) and a catalytic amount of tosic acid monohydrate, followed by acidic workup, yields pure taxol.

CONVERSION OF CEPHALOMANNINE TO N-DEBENZOYLTAXOL

N-Debenzoyltaxol was prepared by reacting N-debenzoyl-N-pyruvyltaxol, 31, with 1,2-diphenylenediamine in the presence of molecular sieves (3 Å) and a catalytic amount of tosic acid monohydrate in refluxing benzene and ethyl acetate for 12 hours to give N-debenzoyltaxol in 72% yield.

CONVERSION OF CEPHALOMANNINE TO TAXOL

Application of the reaction sequence utilizing hydrogenation and conversion to an oxalyl-containing moiety, described above, to pure cephalomannine will yield pure taxol, since the reaction proceeds on a mixture of taxol and cephalomannine to yield a single pure product. In fact, experiments indicate that cephalomannine actually reacts somewhat more readily than taxol in this process.

Figure 7:
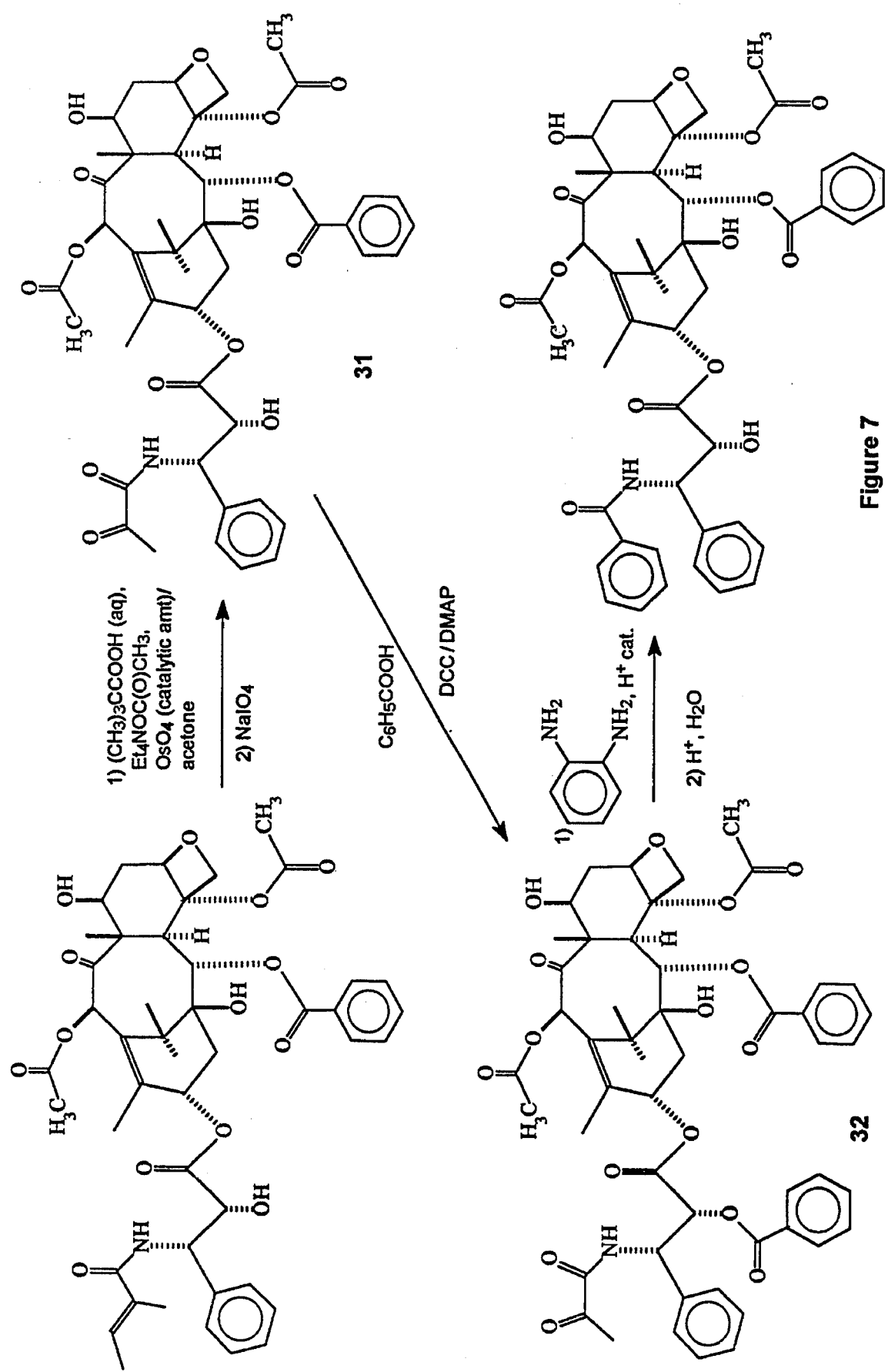
FIG. 7 illustrates the conversion of cephalomannine to taxol by the sequence of: dihydroxylation, oxidative cleavage of the diol, benzoylation, and reaction with 1,2-phenylenediamine.

In a more preferred embodiment, a mixture of cephalomannine and taxol is converted to taxol without hydrogenating the cephalomannine. A nonlimiting example of this process is illustrated in FIG. 7. Cephalomannine, or the cephalomannine in a mixture of cephalomannine and taxol is oxidized to produce 3'-N-debenzoyl-3'-N-pyruvyltaxol, compound 31. This oxidation may either be done directly, by

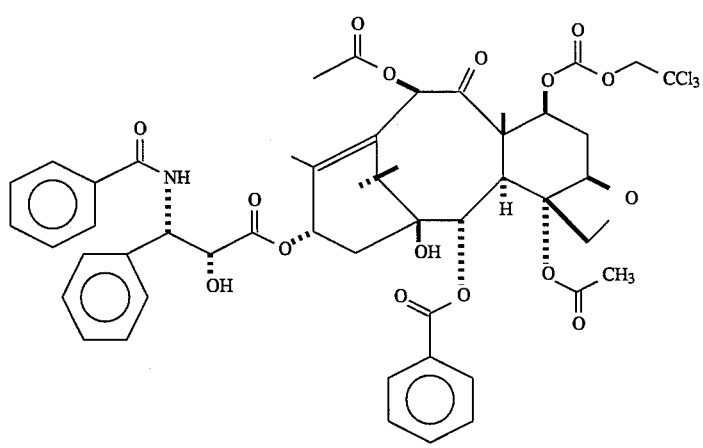

PREPARATION OF ALKYL OXALATE ANALOGS OF TAXOL

Either pure taxol, hydrogenated cephalomannine, or a mixture comprising either or both of these compounds is protected at the 2' and 7 positions by a protecting group, and then converted as described previously to the 2', 7-protected analog of the iminio ion 7. For example, use of the 2,2,2-trichloroethoxycarbonyl ("troc") protecting group results in formation of the 2', 7-bis(2,2,2-trichloroethoxycarbonyl) derivative of the aforementioned compounds. This derivative is then converted as previously described to the 2',7-bis(2,2,2-trichloroethoxycarbonyl) analog of the iminio ion 7. Treatment of the iminio compound with methanol converted it to the N-debenzoyl-N-(methyloxalyl) taxol analog 14. The use of other alcohols, ROH, in the

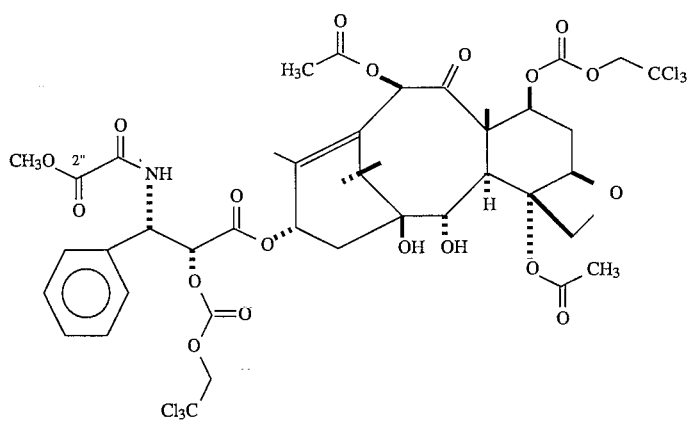

14 quench process allows for the synthesis of analogs of compound 14, where the choice of alkoxy group at the 2' position of the C-13 side-chain is made by selection of the appropriate quench alcohol. The critical feature of this reaction is the presence of the nucleophilic OH group. Although, in a preferred embodiment, R is $CH_3$, the quench alcohol R-OH, may include, but is not limited to, any alkyl, arene, aryl or substituted alkyl or aryl. Illustrative, non-limiting examples of R are phenyl, methylphenyl, methoxyphencyl, hydroxyphenyl, trimethoxyphenyl, chlorophenyl, nitrophenyl, aminophenyl, phenacetyl, methyl, ethyl, and t-butyl. If the quench alcohol in the above reaction is replaced by a metal hydroxide, or if the acidic proton of the oxamic acid derivative is replaced by ion exchange, then R can also be a metal such as sodium or potassium. In preferred embodiments, analogs of compound 14 are useful as anticancer agents when provided in an antineoplastically effective amount, although this may require deprotection of the C-2' and/or C-7 position to optimize such bioactivity.

An alternative preparation of analogs such as 14 is by quenching the iminio derivative with water to yield the ditroc analog 8, followed by treatment of this acid with an alcohol such as methanol and dilute mineral acid or dicyclohexylcarbodiimide (DCC). This alternate procedure is preferred for alcohols other than methanol.

The protecting group at the C-2' and C-7 positions can be removed by reaction with the appropriate reagent. For example, reaction of 14 with Zn in acetic acid converts it to the taxol analog 15.

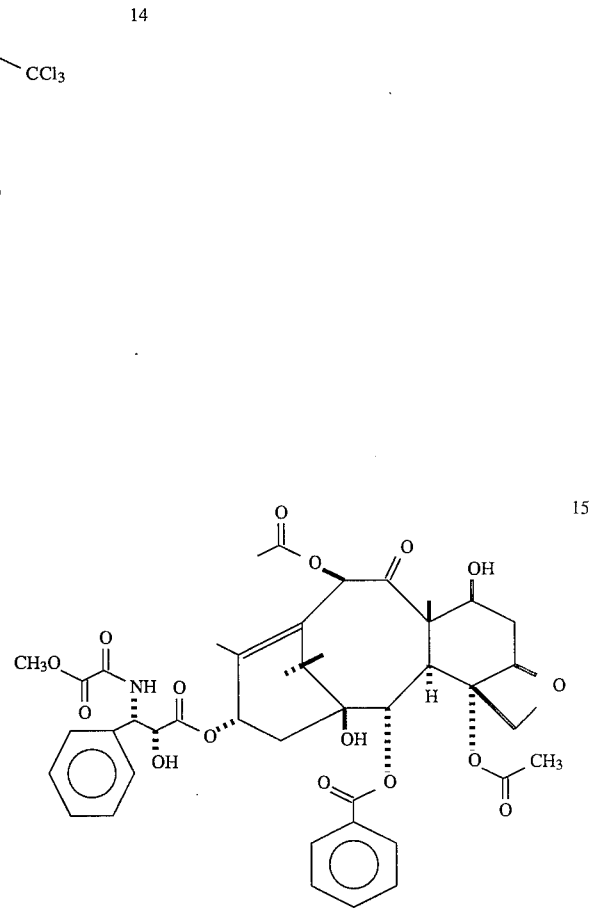

PREPARATION OF N-ALKYL OXAMIDO ANALOGS OF TAXOL

Either pure taxol, hydrogenated cephalomannine, or a mixture comprising either or both of these compounds is protected at the 2' and 7 positions by a protecting group and then converted as described previously to the 2', 7-protected analog of the iminio ion 7. For example, use of the 2,2,2-trichloroethoxycarbonyl protecting group results in formation of the 2', 7-bis(2,2,2-trichloroethoxycarbonyl) analog of the iminio ion 7. Treatment of this hydrogenated compound with an amine, such as by way of non-limiting example, aniline, forms the N-debenzoyl-N-(N'-phenyloxamide) analog 16 where R=Ph.

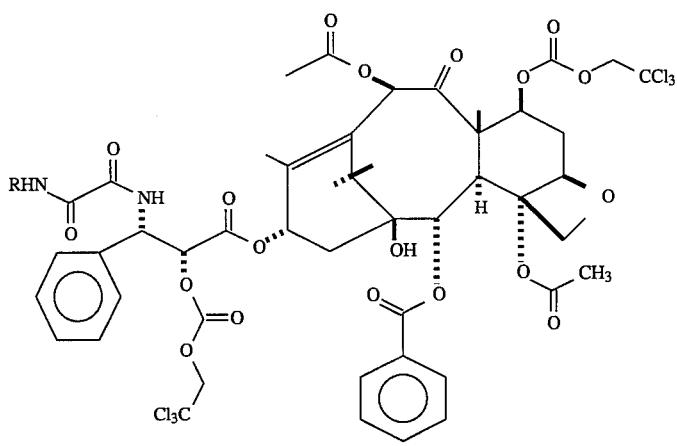

16

The use of other amines in the quench process allows the synthesis of any desired amide analog of compound 16, where the choice of amide, C(O)NHR, is made by the selection of the appropriate amine. Thus, R can be, but is not limited to, any alkyl, alkene, alkyne, aryl or substituted alkyl, alkene, alkyne, or aryl. Preferred analogs of compound 16 are useful as anticancer agents, when administered in an antineoplastically effective amount.

An alternate preparation of analogs such as 16 is by quenching the iminio derivative with water to yield the ditroc analog of 8, followed by treatment of this acid with an amine in the presence of DCC. This alternate procedure is preferred for amines other than analine.

The protecting group at the 2' and 7 positions can be removed by reaction with the appropriate reagent. For example, reaction of 16 with zinc in acetic acid converts it to the taxol analog 17.

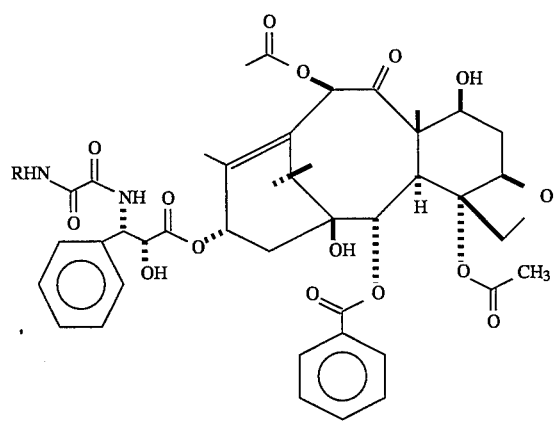

17

Analogs of compounds 14, 15, 16, and 17 that have an acyl group at the C-2' position are obtained by the reaction of taxol or cephalomannine or a mixture containing either or both of these compounds with an acylating reagent (e.g. benzoic acid, See FIG. 1). The resulting compound, 18, is shown below. See also, Holton, U.S. Pat. No. 5,015,744, which shows other taxol analogs, acylated at the 2' position or the 2' and 7 position, which it has been discovered are suitable for use as starting materials for producing the oxalate and oxamido derivatives of the present invention.

The most reactive hydroxyl group at the 2' position will be acylated in preference to the other hydroxyl groups on the taxol or cephalomannine structure. As shown in the synthesis of 14, where the acylating reagent is 2,2,2-trichloroethyl chloroformate, conditions for acylating both positions are readily available.

Appropriate acylating reagents include, but are not limited to: carboxylic acids, carboxylic esters, anhydrides, cyclic anhydrides, amides, lactams, lactones, acid halides (also known as acyl halides), isocyanates and the substituted derivatives of these compounds. Acylation reactions sometimes require activating agents such as tertiary amines and n-butyllithium. Numerous additional acylating reagents and activating agents not specifically recited here can also be used in the present invention.

CONVERSION OF TAXOL OR CEPHALOMANNINE TO N-ACYL ANALOGS OF TAXOL

The method of the present invention as described above can be used to prepare N-acyl taxol analogs. For example, treatment of taxol with a desired acylating reagent will convert it to a 2'-acyltaxol derivative 18. Protection of

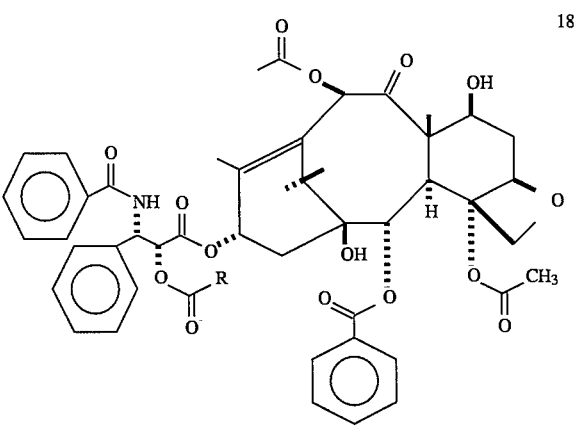

18 at the C-7 position with 2,2,2-trichloroethylchloroformate will yield the protected

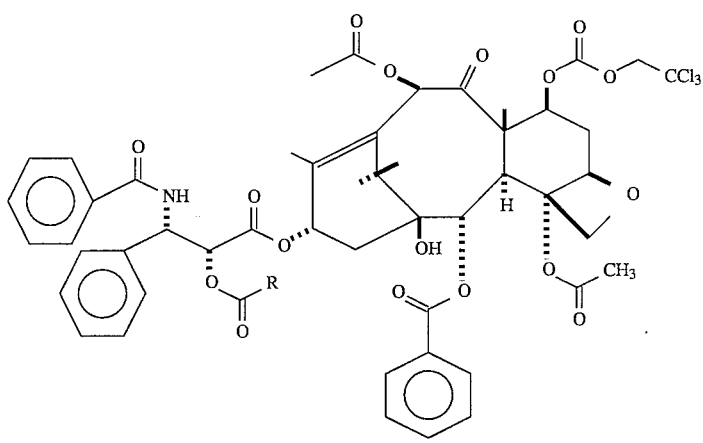

19 derivative 19, and treatment of 19 with oxalyl chloride followed by water as previously described will yield the oxamic acid derivative 20, where R is any desired aryl, lower alkyl, alkenyl or alkynyl or substituted aryl or substituted alkyl group. By way of non-limiting examples, R is phenyl, hydroxyphenyl, methylphenyl, methoxyphenyl, trimethoxyphenyl, chlorophenyl, nitrophenyl, acylphenyl, phenacetyl, methyl, ethyl, and ethynyl. Treatment of 20 with diphenylcarbodiimide, as previously described, will yield the N-acyl derivative 21 by deoxalylation

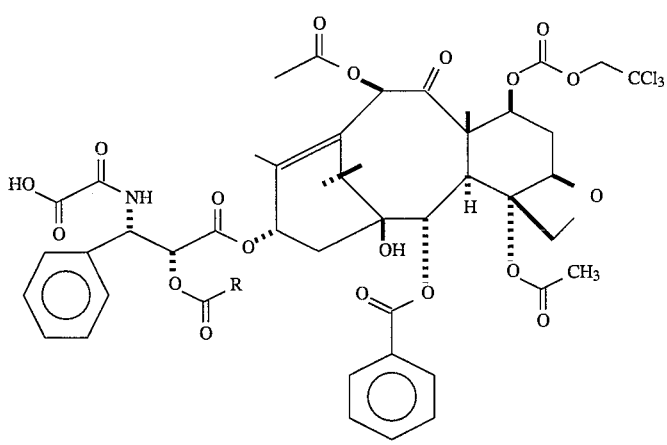

20

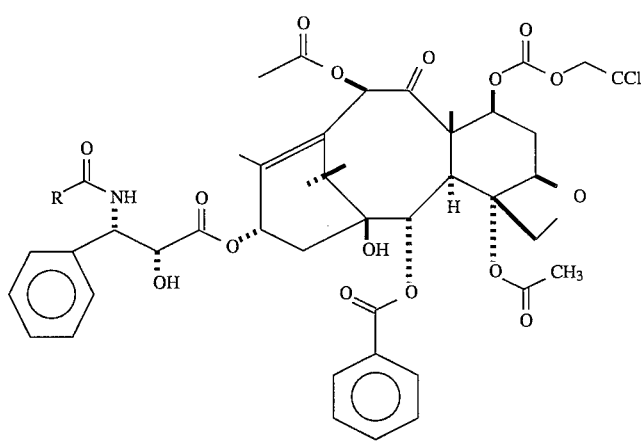

20 followed by O-acyl→N-acyl transfer. Deprotection at C-7 with zinc and acetic acid will then yield the N-acyl taxol analog 22. The same set of reactions could also be carried

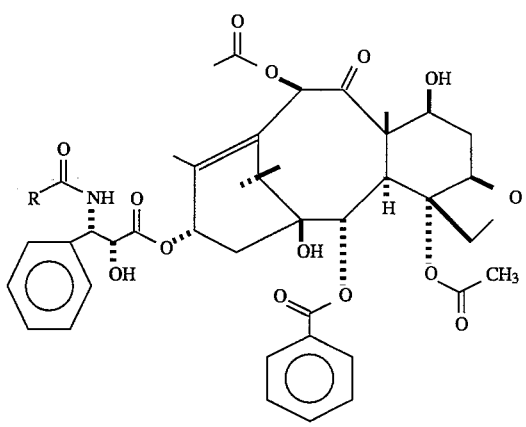

out using hydrogenated cephalomannine in place of taxol, resulting in compounds 20–22 and the 2"-isobutylated analogs of 18 and 19.

In a preferred embodiment, cephalomannine is converted to N-acyltaxol or N-acyltaxol analogs. In this process the tigloyl group of cephalomannine is converted to a pyruvyl group, and the pyruvyl group is replaced by reaction with a compound having adjacent amine groups. In the process described above, acylation of the C-2' hydroxyl group can be accomplished at any of several stages including: acylation of cephalomannine and acylation of the pyruvyl derivative.

In another preferred embodiment, N-acyl taxol derivatives can be made by reacting N-debenzoyltaxol or an N-debenzoyltaxol analog with an acylating agent. Nonlimiting examples of acylations suitable for use in the present invention include: reaction with carboxylic acids, typically in the presence of activating agents such as DCC and DMAP, reaction with acid chlorides, and reaction according to the Schotten-Baumann method. See, for example, Georg et al, "Schotten-Baumann Acylation of N-Debenzoyltaxol; An Efficient Route to N-Acyl Taxol Analogues and Their Biological Evaluation," Bioorg. Med. Chem. Lett., 4, 335–338 (1994). Preferred N-debenzoyl-N-acyltaxol analogs of the present invention have the structure:

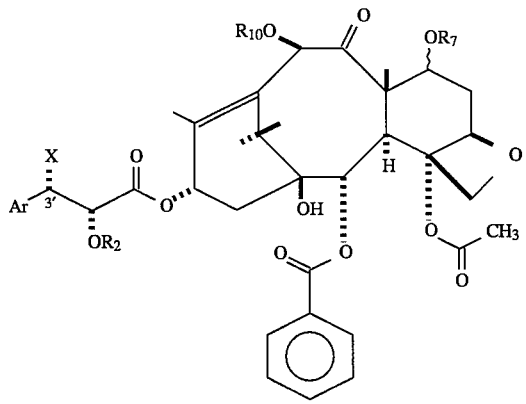

wherein X is an amide, $R_2$ is an acyl, hydrogen, or a protecting group such as triethylsilyl; $R_7$ is hydrogen, acyl, or a protecting group; and $R_{10}$ is hydrogen or an acyl. Multiple examples of various taxol analogs substituted at the C-2', C-7 and C-10 positions are known. See Kingston "The Chemistry of Taxol," *Pharmac Ther.*, 52 1–34, (1991). In especially preferred embodiments, X has the structure:

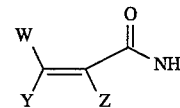

wherein W is hydrogen, lower alkyl, or halogen; Y is hydrogen or lower alkyl; and Z is hydrogen or halogen.

BIOLOGICAL ACTIVITY

As shown in Table 4, the activities of several N-debenzoyl-N-acyltaxols were determined in a cell culture assay using P-388 lymphocytic leukemia cells, and compared with that of taxol; compounds with an $ED_{50}\backslash ED_{50}$ (taxol) value of less than 1 are more active than taxol in this assay, but any activity is significant since the activity in other cell lines and especially in taxol-resistant cell lines may be better than that of taxol. N-debenzoyl-N-acyltaxol analogs having the structure for X shown in the previous two figures, which showed increased activity compared with taxol in the P-388 assay, had the formulas shown above wherein: W is methyl and Y and Z are hydrogen; W and Y are hydrogen and Z is bromine; and W and Z are bromine and Y is methyl. For details of the cell culture assay, see Abbott, B. J., "Protocol 14 of Instruction 275," National Cancer Institute, National Institutes Of Health, Jan. 24, 1978. N-acyltaxol analogs are important analogs of taxol for anticancer treatment. The present invention provides a simple way of preparing such analogs from taxol or cephalomannine without removing the C-13 side-chain.

preparation of taxotere from cephalomannine

Hydrogenation of cephalomannine 2, to its dihydro derivative 4 can be followed by protection as the 2'-trichloroethoxy methyl ether (TCEM)-7-troc derivative 23. Other protecting groups can also be used in place of the TCEM and troc derivatives Treatment of 23 or other 2', 7 protected analogs with oxalyl chloride followed by an aqueous

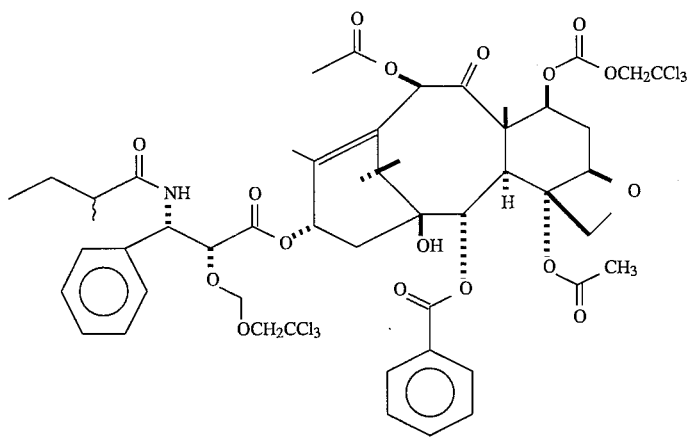

23 quench and subsequent reaction with diphenylcarbodiimide as previously described would give the amino derivative 24.

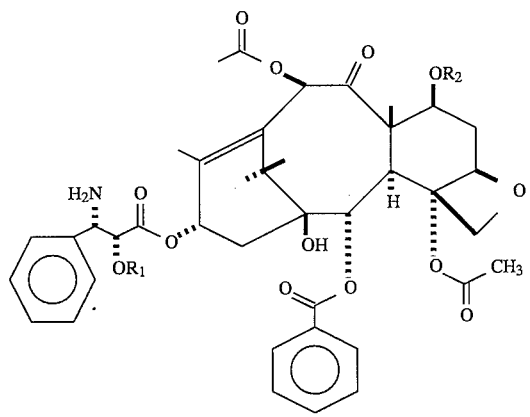

24 R₁=TMEC, R₂=troc or other protecting group

Compound 24 can then be reacted with di-t-butyl dicarbonate to yield the 10-acetyl taxotere derivative 25. The 10-acetyl group of 25 can be hydrolyzed under mild base conditions to yield 26, and deprotection of 26 by zinc and acetic acid will yield taxotere 27. Alternatively, 25 can be deprotected first with zinc and acetic acid to yield 10-acetyl taxotere 28, and this can be hydrolyzed under very mild conditions with methanolic sodium bicarbonate to yield taxotere 27.

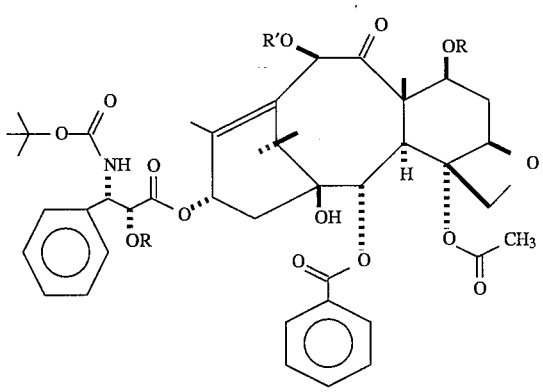

25 R=TCEM or troc or other protecting group, R'=CH₃CO

26 R=TMEC or troc or other protecting group, R'=H
27 R=H, R'=H
28 R=H, R'=CH₃CO

EXAMPLES

The following nonlimiting examples provide specific synthetic methods for the conversion of a mixture of taxol and cephalomannine into pure taxol or N-acyl analogs of taxol. Other methods and materials similar or equivalent to those described herein can be used in the practice or testing of the present invention. Proton NMR data for selected compounds is shown in Tables 1–3.

EXAMPLE 1

Hydrogenation of taxol/cephalomannine

A 262 mg quantity of an approximately 50/50 mixture of taxol and cephalomannine was dissolved in 10 mL of ethyl acetate in a 100 mL round bottom flask with magnetic stirring. Then 20 mg of $PtO_2$ was added and the flask was attached to a hydrogenation apparatus. After flushing the flask five times with hydrogen gas, the solution was stirred at room temperature. After 1 hour, the flask was removed from the hydrogenation apparatus and the solution filtered through Celite to remove the catalyst. The resulting solution was evaporated to dryness under vacuum. The result was 262 mg (100%) of a mixture of taxol and dihydrocephalomannine. No further purification was performed and the sample was used as is in the next step.

2'-Benzoyl-taxol/hydrocephalomannine

A 251 mg quantity of a taxol and dihydrocephalomannine mixture was dissolved in 10 mL of dry acetonitrile in a 50 mL round bottom flask that had been flushed with argon gas and equipped with magnetic stirring. To this solution, 41 mg of benzoic acid and 94 mg of dicyclohexylcarbodiimide were added. Finally, a few crystals of 4-dimethylaminopyridine were added. The solution was stirred at room temperature, and the reaction was monitored using TLC (Kieselgel 60 $F_{254}$, 6:4 ethyl acetate/hexane). After 5 hours the reaction was stopped by evaporating the solvent under vacuum. The crude product was purified by flash chromatography using 230–400 mesh silica gel 60 (250 mm×25 mm bed with a 9:1 chloroform/acetone eluent). The result was 268 mg (95%) of 2'-benzoyl taxol/dihydrocephalomannine.

2'-Benzoyl-7-(2,2,2-trichloroethyloxycarbonyl) taxol/dihydrocephalomannine

A 244 mg quantity of a 50/50 mixture of 2'-benzoyl taxol and 2'-benzoyl dihydrocephalomannine was dissolved in 10 mL of dry methylene chloride in a 50 mL round bottom flask that had been flushed with argon gas. Then 54 μL of 2,2,2-trichloroethylchloroformate and 32 μL of dry pyridine were added. The solution was stirred at room temperature using magnetic stirring. The reaction was monitored by TLC (Kieselgel 60 $F_{254}$, 9:1 chloroform/acetone). After 24 hours, the solution was diluted with 50 mL of ethyl acetate and washed with 2N HCl (2×50 mL), water (2×50 mL), and brine (1×50 mL). After drying with magnesium sulfate, the solvent was removed under vacuum. The crude product was purified by flash chromatography using 230–400 mesh silica gel 60 (250 mm ×25 mm bed with a 9:3:1 chloroform/hexane/acetone eluent). The result was a yield of 246 mg (85%) of 2'-benzoyl-7- (2,2,2-trihloroethyloxycarbonyl) taxol/dihydrocephalomannine.

2'-Benzoyl-7,(2,2,2-trichloroethyloxycarbonyl)-N-debenzoyl-N-oxaeyl taxol

A 228 mg quantity of 2'-benzoyl-7-(2,2,2-trichloroethyloxycarbonyl) taxol/dihydrocephalomannine was dissolved in HPLC grade benzene in a 25 mL round bottom flask, which had been flushed with argon gas and equipped with a magnetic stirrer. To this solution, 54 μL of oxalyl chloride was added, and the resulting solution was stirred at room temperature. After 5 hours an additional 54 μL of oxalyl chloride was added. After 12 hours, the reaction was quenched by the addition of 5 mL of acetone and 1 mL of water. The solution was stirred for 1 additional hour, and then the solvent was removed under vacuum. The crude product was purified using a preswelled Sephadex LH-20 chromatographic support (250 mm×25 mm bed). The column was eluted with 50 mL of methylene chloride followed by 100 mL of 9:1 methylene chloride/acetone. The result was a yield of 147 mg (65%) of 2'-benzoyl-7-(2,2,2-trichloroethyloxycarbonyl)-N-debenzoyl-N-oxalyl taxol.

7-(2,2,2-trichloroethyloxycarbonyl) taxol

A 13.7 mg quantity of diphenylcarbodiimide was dissolved in 2 mL of dry methylene chloride in a 15 mL round bottom flask that had been flushed with argon gas. To this solution 52 mg of 2'-benzoyl-7-(2,2,2-trichloroethyloxycarbonyl)-N-debenzoyl-N-oxalyl taxol was added. The reaction was stirred at room temperature and monitored by TLC (Kieselgel 60 $F_{254}$, 6:4 ethyl acetate/hexane). After 96 hours the reaction was stopped by removing the solvent under vacuum. The crude product was purified by preparative TLC (Analtech taperplate, 63:30:7 methylene chloride/hexane/acetone). The result was a yield of 24.5 mg (50%) of 7-(2,2,2-trichloroethyloxycarbonyl) taxol.

Taxol

A 24.5 mg quantity of 7-(2,2,2-trichloroethyloxycarbonyl) taxol was dissolved in 2 Ml of acetic acid and 20 mg of zinc dust was added. The resulting heterogeneous solution was stirred at 40° C. After 2 hours, the solution was filtered to remove the zinc and diluted with 20 mL of ethyl acetate. It was then extracted with saturated sodium bicarbonate (3×20 mL) and water (2×10 mL). The organic layer was dried over magnesium sulfate and the solvent removed under vacuum. The crude product was purified by flash chromatography using 230–400 mesh silica gel 60 (320 mm×15 mm bed with a 1;1 acetone/hexane eluent). The result was 9.5 mg (47%) of taxol.

EXAMPLE 2

2'7-(2,2,2-trichloroethyloxycarbonyl)-N-debenzoyl-N'-phenyloxamido taxol

A 55.5 mg quantity of 2'7-(2,2,2trichloroethyloxycarbonyl) taxol/dihydrocephalomannine was dissolved in 2 mL of HPLC grade benzene in a round bottom flask that had been flushed with argon gas and equipped with a magnetic stirrer. To this solution 20 μL of oxalyl chloride was added and the resulting solution was stirred at room temperature. After 2 hours, an additional 20 μL of oxalyl chloride was added. When 18 hours had passed, another 10 μL of oxalyl chloride was added to drive the reaction to completion. At approximately 20 hours, 0.5 mL of the reaction mixture was quenched by the addition of 2 mL of acetone and 25 μL of aniline. Approximately 1 hour after addition of the acetone-aniline quench, the reaction was stopped by removal of the solvent under vacuum. The crude product was purified by flash chromatography using 230–400 mesh silica gel 60 (320mm×15 mm bed with a 10:9:1 hexane/methylene chloride/acetone eluent). The result was a yield of 12.3 mg (85%) of 2', 7bis(2,2,2-trichloroethyloxycarbonyl)-N-debenzoyl-N'-phenyloxamido taxol.

N-Pyruvyl-N-debenzoyl taxol

A 140.0 mg quantity of a diastereomeric mixture of cephalaomannine diols was dissolved in 5 mL of 80% aqueous methanol in a round bottom flask that had been equipped with a magnetic stirrer. To this solution, a 60 mg quantity of sodium meta-periodate was added and the resulting solution was stirred at room temperature. After 3 hours, the reaction mixture was concentrated on a rotovapor, 20 mL of water added and the flask left in a refrigerator (at 4° C.) for 12 hours. The resulting white precipitate was filtered at the pump and dried under vacuum to obtain 104 mg of a colorless powder. The filtrate was diluted with 10 mL of water and extracted three times with dichloromethane (3×10 mL). Dichloromethane extracts were washed with water (3×5 mL), dried over anhydrous sodium sulfate and evaporated under vacuum to yield 20 mg of a white solid. The result was a total yield of 124 mg (89%) of chromatographically pure N-pyruvyl-debenzoyl taxol.

2'-Benzoyl-N-pyruvyl-N-debenzoyl taxol

A 60.0 mg quantity of N-pyruvyl-N-debenzoyl taxol was dissolved in 1.0 mL of HPLC grade ethyl acetate in a round bottom flask that had been evacuated and flushed with argon gas and equipped with a magnetic strirrer. To this solution, 23.0 mg of dicyclohexyl carbodiimide, 12.0 mg of recrystallized benzoic acid and 1.0 mg of 4-dimethylaminopyridine were added and the resulting solution was stirred at room temperature. After 24 hours, 10.0 mL of ethyl acetate was added and the mixture filtered through a plug of silica gel 60. The crude product was purified by preparative TLC (Analtech; silica gel; 1000 mM; 20×20 cm, 50:50 hexane/ethyl acetate). The result was a yield of 62.0 mg (92%) of 2'-benzoyl-N-pyuvyl-N-debenzoyl taxol.

Taxol.

A 23.0 mg quantity of 2'-benzoyl-N-pyruvyl-N-debenzoyl taxol was dissolved in 2.5 mL of anhydrous benzene. To this solution 27.0 mg of 1,2-phenylenediamine (which had been recrystalized from hot water and thoroughly dried), 4.0 mg of p-toluenesulfonic acid monohydrate and 5 balls of 4 Å molecular sieves were added. The resulting heterogeneous solution was refluxed under argon. After 2 hours, 10 mL of ethyl acetate was added and the solution was filtered to remove the molecular sieves. It was then washed with 10% aqueous hydrochloric acid (3×5 mL) and saturated brine (3×5 mL). The organic layer was dried over anhydrous sodium sulfate and the solvents removed under vacuum. The crude product was purified by preparative TLC (Analtech; silica gel, 1000 mM, 20×20 cm; 60:40 ethyl acetate/hexane). The result was 20.9 mg (91%) of taxol, identical with authentic material by TLC and $^1$H-NMR.

2'-(3,4,5-trimethoxybenzovoyl)-N-pyruvyl-N-debenzoyl taxol

A 19.0 mg quantity of N-pyruvyl-N-debenzoyl taxol was dissolved in 0.5 mL of HPLC grade ethyl acetate in a round bottom flask that had been evacuated and flushed with argon gas and equipped with a magnetic stirrer. To this solution, 10.0 mg of dicyclohexylcarbodiimide, 7.5 mg of recrystallized 3,4,5-trimethoxybenzoic acid and 1.0 mg of 4-dimethylaminopyridine were added and the resulting solution was stirred at room temperature. After 5 hours, 10.0 mL of ethyl acetate was added and the mixture filtered through a plug of silica gel 60. The crude product was purified by preparative TLC (Analtech; silica gel; 1000 mM, 20×20 cm, 60:40 ethyl acetate/hexane). The result was a yield of 17.8 mg( 76%) of 2'- (3,4,5-trimethoxy)benzoyl-N-pyruvyl-N-debenzoyl taxol.

N-(3,4,5-trimethoxybenzoyl)-N-debenzoyl taxol

A 6.0 mg quantity of 2'-(3,4,5-trimethoxybenzoyl)-N-pyruvyl-N-debenzoyl taxol was dissolved in 0.5 mL of anhydrous benzene. To this solution 10.0 mg of 1,2-phenylenediamine (which had been recrystallized from hot water and thoroughly dried), 1.0 mg of p-toluenesulfonic acid monohydrate and 2 balls of 4 Å molecular sieves were added. The resulting heterogeneous solution was refluxed under argon. After 1 hour, 10 mL of ethyl acetate was added and the solution was filtered to remove the molecular sieves. It was then washed with 10% aqueous hydrochloric acid (3×5 mL) and saturated brine (3×5 mL). The organic layer was dried over anhydrous sodium sulfate and the solvents removed under vacuum. The crude product was purified by preparative TLC (Analtech; silica gel, 500 mM, 20×20 cm; 60:40 ethyl acetate/hexane, 2 elutions). The result was 5.0 mg (83%) of N-(3,4,5-trimethoxybenzoyl)-N-debenzoyl taxol.

TABLE 1

$^1$H NMR OF DERIVATIVES OF TAXOL/ CEPHALOMANNINE MIXTURES

| Protons on | Mixture of (1) and (4) | Mixture of (6) and (6) |
|---|---|---|
| C-2 | 5.68 (d,7) | 5.70[b] |
| C-3 | 3.78 (m) | 3.95 (d,8) |
| C-5 | 4.94 (d,10) | 4.98 (d,11) |
| C-6 | a | a |
| C-7 | 4.40 (m) | 5.59 (m) |
| C-10 | 6.28 (s) | 6.38 (s) |
| C-13 | 6.23 (t,9) | 6.26 (s) |
| C-14 | a | a |
| C-16 | 1.15 (s) | 1.16 (s) |
| C-17 | 1.25 (s) | 1.21 (s) |
| C-18 | 1.79 (s) | 1.83 (s) |
| C-19 | 1.66 (s) | 1.66 (s) |
| C-20α | 4.30 (d,6) | 4.33 (d,8) |
| C-20β | 4.19 (d,6) | 4.19 (d,8) |
| C-2' | (T) 4.79 (dd) | 5.69[b] |
|  | (C) 4.69 (m) | a |
| C-3' | (T) 5.80 (dd,7,1) | (T) 6.05 |
|  | (C) 5.58 (m) | (C) 5.90 |
| 3'-NH | (T) 7.05 (d,8) | (T) 7.05 (d,8) |
|  | a | (C) 6.26[b] |
| 4-OAc | 2.48 (s) | 2.45 (s) |
| 10-OAc | 2.24 (s) | 2.15 (s) |
| 2-OBz,3'-NBz, 3¹-Ph | 7.35–8.15 | 7.38–8.12 |
| 7-OCOOCH$_2$CCl$_3$ |  | 5.02 (d,12) |
|  |  | 4.65 (d,12) |
| 2'-OBz |  | 7.38–8.01 |
| CH$_3$CH$_2$CH(CH$_3$)CO | 0.90–2.50[c] | 0.90–2.50[c] | a Not determined due to overlapping peaks.

TABLE 1-continued $^1$H NMR OF DERIVATIVES OF TAXOL/ CEPHALOMANNINE MIXTURES

| Protons on | Mixture of (1) and (4) | Mixture of (6) and (6) |
|---|---|---|

[b]Difficult to determine exact chemical shift due to overlapping peaks.
[c]The exact chemical shift of the protons on the hydrogenated tigloyl group is difficult to determine not only because they overlap with other peaks but also because hydrogenation of the tigloyl group creates a chiral center which leads to two disastereomers resulting in a very complex pattern.
(T) = taxol
(C) = cephalomannine

TABLE 2

$^1$H NMR SPECTRA OF TAXOL DERIVATIVES

| Proton on | Compound (8) | Compound (13) | Compound (17) |
|---|---|---|---|
| C-2 | 5.65[b] | 5.68 (d,7) | 5.64 (d,7) |
| C-3 | 3.95 (d,7) | 3.95 (d,7) | 3.79 (d,7) |
| C-5 | 4.95 (d,10) | 4.95 (d,10) | 4.93 (d,7) |
| C-6 | a | a | a |
| C-7 | 5.65[b] | 5.54 (m) | 4.39 (t,7) |
| C-10 | 6.35 (s) | 6.24 (s) | 6.25 (s) |
| C-13 | 6.17 (t,8) | 6.20 (t,8) | 6.25 (t,10) |
| C-14 | a | a | a |
| C-16 | 1.14 (s) | 1.17 (s) | 1.12 (s) |
| C-17 | 1.21 (s) | 1.25 (s) | 1.22 (s) |
| C-18 | 1.96 (s) | 1.85 (s) | 1.87 (s) |
| C-19 | 1.81 (s) | 1.84 (s) | 1.67 (s) |
| C-20α | 4.34 (d,8) | 4.34 (d,8) | 4.29 (d,8) |
| C-20β | 4.17 (d,8) | 4.18 (d,8) | 4.17 (d,8) |
| C-2' | 5.65[b] | 4.79 (d,3) | 4.71 (d,8) |
| C-2 | 5.65[b] | 5.79 (dd,9,3) | 5.57 (dd,10,3) |
| 3'-NH | 8.15[b] | 7.05 (d,9) | 8.37 (d,10) |
| 4-OAc | 2.35 (s) | 2.39 (s) | 2.37 (s) |
| 10-OAc | 2.17 (s) | 2.17 (s) | 2.22 (s) |
| 2'-OB$_2$, 3'-pH 7-OCOO | 7.35–8.20 | 7.39–8.13 | 7.28–8.10 |
| CH$_2$CCl$_3$ | 5.05 (d,12)[c] | 5.03 (d,12)[c] |  |
|  | 4.67 (d,12)[c] | 4.64 (d,12)[c] |  |
| 2'-OBz | 7.40–7.65[b] |  |  |
| 3'-NBz |  | 7.39–7.77[b] |  |
| oxalyl-NH |  |  | 8.98 (s) |
| N—Ph |  |  | 7.24–7.61(cm)[b] | a Not determined due to overlapping peaks.
[b]Difficult to determine exact chemical shift due to overlapping peaks.
c The two protons on the troc group are diastereotopic.

TABLE 3

$^1$H NMR SPECTRA OF TAXOL

| Proton | Taxol (Prepared) | Taxol (Literature)[1] |
|---|---|---|
| C-2 | 5.67 (d,7) | 5.67 (d,7.1) |
| C-3 | 3.80 (d,7) | 3.79 (dd,7.1,1.0) |
| C-5 | 4.94 (d,8) | 4.94 (ddt,9.6,2.3,1) |
| C-6 | a |  |
| C-7 | 4.40 (m) | 4.40 (ddd,10.9,6.7,4.3) |
| C-10 | 6.27 (s) | 6.27 (s) |
| C-13 | 6.23 (t,8) | 6.23 (tq,9.0,1.5) |
| C-14 | a |  |
| C-16 | 1.14 (s) | 1.14 (s) |
| C-17 | 1.25 (s) | 1.24 (s) |
| C-18 | 1.79 (s) | 1.79 (d,1.5) |
| C-19 | 1.68 (s) | 1.68 (s) |
| C-20α | 4.30 (d,8) | 4.30 (ddd,8.4,1.1,0.8) |
| C-20β | 4.19 (d,8) | 4.19 (dd,8.5,1.0) |
| C-2' | 4.79 (br s) | 4.78 (dd,5.4,1.0) |
| C-3' | 5.79 (dd,9,3) | 5.78 (33,8.9,2.8) |
| C'—NH | 6.99 (d,9) | 7.01 (d,8.9) |
| 4-OAc | 2.39 (s) | 2.38 (s) |

TABLE 3-continued

<sup>1</sup>H NMR SPECTRA OF TAXOL

| Proton | Taxol (Prepared) | Taxol (Literature)[1] |
|---|---|---|
| 10-OAc | 2.24 (s) | 2.23 (s) |
| OBz,NBz,3'-Ph | 7.32–8.15 | 7.35–8.13 | a Not determined due to overlapping peaks.
[1]Beutler et al. J. Nat. Prod. 55, 414 (1992).

TABLE 4

CYTOTOXICITY OF N-DEBENZOYL-N-ACYLTAXOLS

| N-Acyl Group | Relative Cytotoxicity in P-388 Cell Culture[a] |
|---|---|
| $CH_3C(Br)=C(CH_3)CO$ | 2.8 |
| $CH_3CHBrCBr(CH_3)CO$ | 10 |
| $PhCH_2OCOCO$ | 97 |
| PhNHCOCO | 7 |
| $CH_3CH_2CH(CH_3)CO$ | 10 |
| $CH_3CH=CHCO$ | 0.05 |
| $CH_3CH=CBrCO$ | 0.002 |
| $Br_2CHCO$ | 17 |
| $CH_3COCO$ | 14 |
| PhCOCO | 10 |
| $CH_3OCOCO$ | 20 |
| O-bromobenzoyl | 25 |
| O-chlorobenzoyl | 4.5 |
| O-nitrobenzoyl | 45 |

*Cytotoxicity is recorded as $ED_{50}$ value relative to taxol determined in the same assay. Absolute $ED_{50}$ of taxol is approximately 0.03 µg/mL in this assay.

TABLE 5

<sup>1</sup>H NMR SPECTRA OF
N-PYRUVYL-N-DEBENZOYLTAXOL DERIVATIVES

| Proton on | Compound (31) | Compound (32) |
|---|---|---|
| C-2 | 5.66 (d,7) | 5.64 (d,7) |
| C-3 | 3.79 (d,7) | 3,78 (d,7) |
| C-5 | 4.94 (d,7.8) | 4.93 (d,8.0) |
| C-7 | 4.40 (dd,11.7) | 4.40 (dd,11.7) |
| C-10 | 6.28 (s) | 6.25 (s) |
| C-13 | 6.22 (t,8.9) | 6.20 (t,9) |
| C-16 | 1.15 (s) | 1.10 (s) |
| C-17 | 1.25 (s) | 1.23 (s) |
| C-18 | 1.80 (br s) | 1.85 (br s) |
| C-19 | 1.68 (s) | 1.65 (s) |
| C-20α | 4.18 (d,8.3) | 4.15 (d,S) |
| C-20β | 4.30 (d,8.3) | 4,28 (d,8) |
| C-2' | 4.68 (d,2.6) | 5.55 (d,2.6) |
| C-3' | 5.49 (dd,7,2.6) | 5.70 (dd,7,2.6) |
| 3'-NH | 7.80 (d,7) | 7.80 (d,7) |
| 4-OAc | 2.39 (s) | 2.40 (s) |
| 10-OAc | 2.25 (s) | 2.20 (s) |
| 2-OBz | 7.32–8.13 (m) | 7.30–8.15 (m) |
| 3'-Ph | 7.32–8.13 (m) | 7.30–8.15 (m) |
| 2'OBz | — | 7.30–8.15 (m) |
| $CH_3COCO-N$ | 2.35 (s) | 2.35 (s) |

The compounds and methods of the present invention are not limited to the specific examples discussed in the section entitled Detailed Description of the Invention. The methods of the present invention are broadly applicable and can be used to prepare a large variety of taxol and baccatin III analogues having amides at the C-3' position as disclosed herein. A wide array of taxol and baccatin III analogues may be used as starting materials in the methods of the present invention. This invention further contemplates reactions, such as acylations, prior to and subsequent to N-acylation, which can produce a wide variety of compounds. Various synthetic steps such as protecting steps (for example at the C-2' and C-7 positions), and acylating and deacylating steps (for example at the C-2' C-7 and C-10 positions) may be those described herein or those otherwise known in the prior art. The products of the present invention may be prepared as either desired final products, or as intermediates in the synthesis of desired taxol analogues.

It is contemplated that substituents on the tetracyclic taxane nucleus be selected based upon the medicinal or synthetic characteristics that various substituents will impart to the taxol analogue. Workers of ordinary skill in the chemical and pharmaceutical arts will appreciate that the widely applicable methods of the present invention enable the strategic selection of substituents (from a very large number of possible substituents which could be placed on the tetracyclic taxane nucleus) at certain locations on the taxane tetracyclic nucleus.

From the above teachings it is apparent that many modifications and variations of the present invention are possible. It is therefore to be understood that the invention may be practiced otherwise than as specifically described.

We claim:

1. Compounds having the following structure:

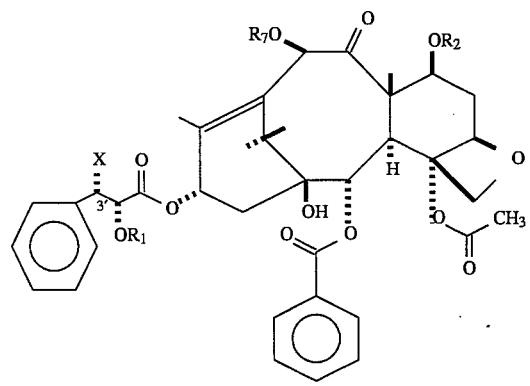

wherein:
$R_1$ and $R_2$ are independently H, $Si(CH_3)_3$, $Si(C_2H_5)_3$ or acyl, and X is selected from the group comprised of:

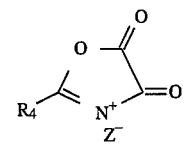

and NHY; wherein $R_4$ is an alkyl, or aryl, and Y is selected from the group consisting of $C(O)C(O)OR_5$ and $C(O)C(O)NHR_6$ wherein:
$R_5$ is hydrogen, an alkali metal, an alkyl, an alkenyl, an alkynyl, or an aryl;
$R_6$ is hydrogen, an alkyl, an alkenyl, an alkynyl, or an aryl; and
$R_7$ is selected from the group consisting of H and $CH_3C(O)$; and $Z^-$ is a counter ion.

2. The compound of claim 1, where $R_1$ and $R_2$ are independently hydrogen or an alkanoyl or an aroyl.

3. The compound of claim 1 wherein X is $C(O)C(O)NHC_6H_5$.

4. The compound of claim 1 wherein $R_1$ and $R_2$ are selected from the group consisting of H, $CH_3C(O)$, $COOCH_2CCl_3$ and $C_6H_5C(O)$.

5. The compound of claim 1, wherein X is an iminio ion.

6. The compound of claim 1, wherein $Z^-$ is $Cl^-$.

7. The compound of claim 5, wherein $R_4$ is selected from the group consisting of $C_6H_5$ and $CH_3CH_2CH(CH_3)$.

8. A pharmaceutical composition, comprising an antineoplastically effective amount of a compound of claim 1 as an active ingredient wherein X is NHY and Y is selected from the group consisting of $C(O)C(O)OR_5$ and $C(O)C(O)NHR_4$ wherein $R_5$ is alkyl and $R_4$ is an aryl.

9. Compounds having biological activity and having the structure:

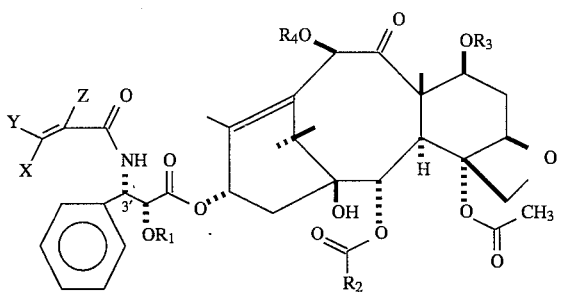

wherein X is selected from the group consisting of hydrogen lower alkyl and halogen; Y is selected from the group consisting of hydrogen and lower alkyl; Z is selected from the group consisting of hydrogen and halogen; provided that when Y and Z are hydrogen, X is not lower alkyl and that at least one of X or is halogen;

and further wherein $R_1$ is selected from the group consisting of hydrogen, acyl, and protecting group; $R_2$ is phenyl, $R_3$ is selected from the group consisting of hydrogen, acyl and protecting group; and $R_4$ is selected from the group consisting of hydrogen and acyl.

10. The compounds of claim 9 wherein $R_1$ is hydrogen.

11. The compounds of claim 9 wherein $R_3$ is hydrogen and $R_4$ is selected from the group consisting of hydrogen and acetyl.

12. The compounds of claim 9 wherein $R_3$ is $C(O)OCH_3CCl_3$.

13. The compounds of claim 9 wherein Z is halogen.

14. The compounds of claim 13 wherein X is selected from the group consisting of hydrogen and lower alkyl.

15. The compounds of claim 14 wherein Y is hydrogen, X is lower alkyl, Z is bromine and $R_2$ is phenyl.

16. The compound of claim 15 wherein X is methyl, $R_1$ and $R_3$ are hydrogen and $R_4$ is acetyl.

17. The compounds of claim 9 wherein Z is hydrogen.

18. The compounds of claim 17 wherein $R_4$ is acetyl.

19. The compounds of claim 1 wherein X is $C(O)C(O)OH$; and $R_1$ and $R_2$ are independently H or acyl.

20. The compounds of claim 5 wherein $R_4$ is phenyl.

21. The compounds of claim 20 wherein $R_1$ and $R_2$ are selected from the group consisting of H, $CH_3C(O)$, $COOCH_2CCl_3$ and $C_6H_5C(O)$.

22. The compounds of claim 21 wherein $Z^-$ is $Cl^-$.

* * * * *